US012440411B2

(12) United States Patent
Chang et al.

(10) Patent No.: US 12,440,411 B2
(45) **Date of Patent: *Oct. 14, 2025**

(54) TRANSFER DEVICE WITH PLATFORM PLATE HAVING TWO-SIDED FUNCTIONALITY AND TREATMENT SYSTEM

(71) Applicant: Able Innovations Inc., Toronto (CA)

(72) Inventors: Philip Chang, York (CA); Ngoc Phuong Bui, Toronto (CA); Veronica Guthrie, Toronto (CA); Aidan Muller, Toronto (CA); Cassra Sodeifi, Toronto (CA); Jayiesh Singh, Toronto (CA); Trevor Jordan Vaughan, Toronto (CA)

(73) Assignee: Able Innovations Inc. (CA)

( * ) Notice: Subject to any disclaimer, the term of this patent is extended or adjusted under 35 U.S.C. 154(b) by 243 days.

This patent is subject to a terminal disclaimer.

(21) Appl. No.: 18/061,937

(22) Filed: Dec. 5, 2022

(65) Prior Publication Data

US 2023/0310241 A1 Oct. 5, 2023

Related U.S. Application Data

(63) Continuation-in-part of application No. 17/708,439, filed on Mar. 30, 2022, now Pat. No. 11,628,111.

(51) Int. Cl.
*A61G 7/10* (2006.01)
*A61B 90/70* (2016.01)

(52) U.S. Cl.
CPC ............ *A61G 7/1026* (2013.01); *A61B 90/70* (2016.02); *A61G 2203/10* (2013.01)

(58) Field of Classification Search
CPC .... A61G 1/003; A61G 7/1025; A61G 7/1026; A61G 7/103; A61G 7/1032;
(Continued)

(56) References Cited

U.S. PATENT DOCUMENTS 2,918,681 A 12/1959 Fenimore
2,984,842 A 5/1961 Richards
(Continued)

FOREIGN PATENT DOCUMENTS

CN 1903154 A 1/2007
CN 100493484 C 6/2009
(Continued)

OTHER PUBLICATIONS

Kedar, S.A., et al., "Lateral Transfer Devices for Hospital Stretcher," Applied Mechanics and Materials vols. 446-447 (2014) pp. 1330-1333.

(Continued)

*Primary Examiner* — George Sun
(74) *Attorney, Agent, or Firm* — DENTONS DAVIS BROWN PC; Matthew Warner-Blankenship

(57) ABSTRACT

Disclosed is a transfer device having a device body, a transfer platform including a platform plate, and a platform lateral actuator. The platform lateral actuator is configured to selectively move the platform plate laterally relative to the device body, such that the platform plate can be moved between a plurality of positions including (i) a stowed position in which the platform plate is retracted relative to the device body, (ii) a first extended position in which a first transverse edge of the platform plate is a leading edge that extends outward from a first side of the device body, and (iii) a second extended position in which a second transverse edge of the platform plate is a leading edge that extends outward from a second side of the device body. The transfer device also a treatment system configured to apply a cleaning and/or disinfecting treatment.

22 Claims, 37 Drawing Sheets

(58) Field of Classification Search

CPC ................ A61G 7/1034; A61G 7/1036; A61G 2203/10; A61G 2203/70; A61L 2/10; A61L 2/22; A61L 2202/11; A61L 2202/15; A61L 2202/17; A61B 90/70

See application file for complete search history.

(56) References Cited

U.S. PATENT DOCUMENTS

| | | | | |
|---|---|---|---|---|
| 3,493,979 | A | 2/1970 | Koll et al. | |
| 3,579,672 | A | 5/1971 | Koll et al. | |
| 3,593,351 | A * | 7/1971 | Dove | A61G 7/1057 5/88.1 |
| 3,654,644 | A | 4/1972 | Stevens | |
| 3,765,037 | A | 10/1973 | Dunkin | |
| 3,829,915 | A | 8/1974 | Dunkin | |
| 3,854,152 | A | 12/1974 | Chez | |
| 3,947,902 | A * | 4/1976 | Conde | A61G 7/1046 5/81.1 C |
| 3,967,328 | A | 7/1976 | Cox | |
| 4,073,016 | A | 2/1978 | Koll | |
| 4,109,329 | A * | 8/1978 | Tupper | A61G 7/1046 5/607 |
| 4,125,907 | A * | 11/1978 | Junginger | A61G 7/1019 5/87.1 |
| 4,545,571 | A * | 10/1985 | Chambron | A61B 6/04 5/601 |
| 4,669,137 | A | 6/1987 | Schnelle | |
| 4,680,818 | A | 7/1987 | Ooka | |
| 4,794,655 | A | 1/1989 | Ooka | |
| 4,873,732 | A | 10/1989 | Perez | |
| 4,914,769 | A | 4/1990 | Kume et al. | |
| 5,540,321 | A | 7/1996 | Foster | |
| 5,937,456 | A | 8/1999 | Norris | |
| 6,131,214 | A | 10/2000 | Moenning | |
| 6,499,156 | B1 | 12/2002 | Dirst | |
| 6,854,137 | B2 | 2/2005 | Johnson | |
| 6,857,143 | B2 | 2/2005 | McNulty | |
| 7,200,881 | B2 | 4/2007 | Kasagami et al. | |
| 7,484,252 | B2 | 2/2009 | Wang | |
| 7,540,044 | B2 | 6/2009 | Patterson et al. | |
| 7,578,011 | B2 | 8/2009 | Johnson | |
| 7,861,336 | B2 | 1/2011 | Patterson et al. | |
| 8,214,944 | B2 | 7/2012 | Patterson | |
| 8,307,478 | B2 | 11/2012 | Patterson et al. | |
| 8,356,368 | B2 | 1/2013 | Patterson | |
| 9,254,233 | B2 | 2/2016 | Schy | |
| 9,393,168 | B2 | 7/2016 | Konda | |
| 9,579,243 | B2 | 2/2017 | Rice et al. | |
| 9,668,929 | B2 | 6/2017 | Patterson et al. | |
| 9,730,849 | B2 | 8/2017 | Patterson et al. | |
| 11,744,910 | B1 | 9/2023 | Buckner | |
| 2003/0226202 | A1* | 12/2003 | McNulty | A61G 1/003 5/81.1 HS |
| 2004/0244108 | A1 | 12/2004 | Spanton | |
| 2005/0135907 | A1 | 6/2005 | Romano et al. | |
| 2006/0174405 | A1* | 8/2006 | Johnson | A61G 7/1057 5/81.1 R |
| 2007/0251004 | A1* | 11/2007 | Wang | A61G 7/1019 5/81.1 R |
| 2007/0295339 | A1* | 12/2007 | Mizuno | A61G 7/1057 128/845 |
| 2010/0064431 | A1 | 3/2010 | Kawakami et al. | |
| 2010/0138990 | A1 | 6/2010 | Van Oirschot | |
| 2012/0084914 | A1 | 4/2012 | Patterson et al. | |
| 2012/0291196 | A1 | 11/2012 | Konda | |
| 2013/0319460 | A1* | 12/2013 | Schneider | A61L 2/14 134/1.1 |
| 2014/0123384 | A1 | 5/2014 | White et al. | |
| 2014/0306429 | A1* | 10/2014 | Patterson | A61G 7/0528 280/657 |
| 2015/0007386 | A1 | 1/2015 | Patterson et al. | |
| 2016/0106608 | A1* | 4/2016 | Oh | A61G 7/1034 5/81.1 C |
| 2017/0027795 | A1 | 2/2017 | Asil | |
| 2017/0071808 | A1 | 3/2017 | Wunderlich et al. | |
| 2019/0053966 | A1* | 2/2019 | Pigazzi | A61F 5/30 |
| 2019/0070054 | A1* | 3/2019 | Tee | A61G 7/103 |
| 2019/0240095 | A1* | 8/2019 | Yilmaz | A61G 7/1026 |
| 2020/0405557 | A1 | 12/2020 | Hochman et al. | |
| 2022/0184246 | A1* | 6/2022 | Gudiño Casillas | A61L 2/07 |
| 2023/0030171 | A1* | 2/2023 | Ecker | B08B 13/00 |
| 2023/0148035 | A1* | 5/2023 | Ayala | A61L 2/10 422/24 |
| 2023/0277399 | A1 | 9/2023 | Singh | |

FOREIGN PATENT DOCUMENTS

| | | | |
|---|---|---|---|
| CN | 102525750 | A | 7/2012 |
| CN | 104997606 | A | 10/2015 |
| CN | 105559982 | A | 5/2016 |
| CN | 106420194 | A | 2/2017 |
| CN | 106580602 | A | 4/2017 |
| CN | 107361927 | A | 11/2017 |
| CN | 107411897 | A | 12/2017 |
| CN | 108294889 | A | 7/2018 |
| CN | 108324466 | A | 7/2018 |
| CN | 108324467 | A | 7/2018 |
| CN | 108514486 | A | 9/2018 |
| CN | 108578128 | A | 9/2018 |
| CN | 109009705 | A | 12/2018 |
| CN | 109172208 | A | 1/2019 |
| CN | 109259944 | A | 1/2019 |
| CN | 109259945 | A | 1/2019 |
| CN | 110269758 | A | 9/2019 |
| CN | 110522569 | A | 12/2019 |
| CN | 110623798 | A | 12/2019 |
| CN | 110638581 | A | 1/2020 |
| CN | 111249074 | A | 6/2020 |
| CN | 111772970 | A | 10/2020 |
| CN | 111839910 | A | 10/2020 |
| CN | 112006852 | A | 12/2020 |
| CN | 112006854 | A | 12/2020 |
| CN | 112245171 | A | 1/2021 |
| CN | 113209498 | A | 8/2021 |
| CN | 113244059 | | 8/2021 |
| CN | 113350088 | A | 9/2021 |
| CN | 113413272 | A | 9/2021 |
| CN | 113520735 | A | 10/2021 |
| CN | 114191208 | A | 3/2022 |
| CN | 114209503 | A | 3/2022 |
| DE | 2658649 | A1 | 6/1977 |
| DE | 3446017 | A1 | 6/1986 |
| DE | 3614572 | A1 | 11/1986 |
| DE | 2626638 | C2 | 10/1987 |
| EP | 1480591 | A2 | 12/2004 |
| EP | 2428197 | A1 | 3/2012 |
| EP | 3616665 | A1 | 3/2020 |
| JP | 10033593 | A | 2/1998 |
| NL | 2024253 | B1 | 7/2021 |
| WO | 2001030295 | A1 | 5/2001 |
| WO | 2003070143 | A2 | 8/2003 |
| WO | 2007044231 | A2 | 4/2007 |
| WO | 2009023175 | A1 | 2/2009 |
| WO | 2012099629 | A2 | 7/2012 |
| WO | 2014092416 | A1 | 6/2014 |
| WO | 2018007655 | A1 | 1/2018 |
| WO | 2021072547 | A1 | 4/2021 |
| WO | 2021213405 | A1 | 10/2021 |
| WO | 2022150915 | A1 | 7/2022 |

OTHER PUBLICATIONS

International Search Report and Written Opinion dated Dec. 14, 2022 for corresponding International Application No. PCT/CA2022/050485, 11 pages.

Office Action dated May 20, 2022 for parent U.S. Appl. No. 17/708,439, 6 pages.

Office Action dated Aug. 16, 2022 for parent U.S. Appl. No. 17/708,439, 11 pages.

(56) References Cited

OTHER PUBLICATIONS

Office Action dated Feb. 9, 2023 for parent U.S. Appl. No. 17/708,439, 11 pages.

* cited by examiner

TRANSFER DEVICE WITH PLATFORM PLATE HAVING TWO-SIDED FUNCTIONALITY AND TREATMENT SYSTEM

RELATED APPLICATION

This patent application is a CIP (Continuation in Part) application of U.S. patent application Ser. No. 17/708,439 filed on Mar. 30, 2022. Priority is claimed from U.S. patent application Ser. No. 17/708,439 filed on Mar. 30, 2022, the entire disclosure of which is incorporated by reference.

FIELD OF THE DISCLOSURE

This disclosure relates generally to devices and methods for transferring an object from a position on a first surface, onto a platform of the device, and then onto a second surface (or back to the first surface).

BACKGROUND

Countries around the world are facing an aging problem whereby in the coming decades, the majority of their populations will become dependents rather than of an independent age contributing to society. Coupled with this aging population is a growing number of people that have restricted mobility due to injury, illness, or old age. Being mobile necessitates a means of transportation (from point A to point B) as well as being transferred (from surface A to surface B).

There are various transportation aids that are often used to aid mobility. Examples include walkers, wheelchairs, slings, transfer boards and gantry hoists. Many of these devices have not been updated or improved in decades and as a result, fundamental problems associated with the operation of these transfer methods persist. These included injuries to practitioners, reduced patient health and well-being as a result of interaction with these devices, and induced stress on the health-care sector due to implications of the operation of these devices.

The fact however, is that these devices are greatly needed, as between 30% to 60% of patients in long-term care facilities need assistance with transfer to perform routine tasks such as eating a meal or going to the washroom. Without the aid of these devices, people would remain largely immobile once their health starts to fail. Similar challenges exist when performing routine medical diagnostics or conducting routine transfers with bariatrics patients. In these circumstances some transfers that may be required include (but not limited to), from a gurney to a medical imaging table (e.g. the bed of an MRI or CT scanner), movement of a patient temporarily to perform routine operations (e.g. bed cleaning, obtaining a weight measurement for the patient), or simply re-positioning of their body on their existing surface.

Currently the most popular devices used to assist in patient transfer consist of variations of lifts, slings, and transfer boards and sheets. The lifts among these systems are commonly referred to by their trade name as Hoyer Lifts, Hoyer being a popular manufacturer of these devices. These lifts have been in the market for decades with most innovations focusing on improving or re-packaging existing lift technologies. Current technologies typically place significant strain on a human operator, as they typically require some form of "staging" where a sling (or other strap(s) or harnesses) must be inserted underneath a patient, and then removed from under the patient after a transfer. Furthermore, these devices are often costly and may put heavy burdens on operating budgets of long-term care and health care facilities. These devices are also error prone, which often results in numerous injuries to the individuals being transferred, and in some cases has even resulted in death.

SUMMARY OF THE DISCLOSURE

Disclosed is a transfer device having a device body with a first end, a second end, a first side, and a second side. The transfer device also has a transfer platform including a platform plate and a platform lateral actuator. The platform lateral actuator is configured to selectively move the platform plate laterally relative to the device body, such that the platform plate can be moved between a plurality of positions including (i) a stowed position in which the platform plate is retracted relative to the device body, (ii) a first extended position in which a first transverse edge of the platform plate is a leading edge that extends outward from the first side of the device body, and (iii) a second extended position in which a second transverse edge of the platform plate is a leading edge that extends outward from the second side of the device body. The transfer device also has a transfer belt having a first end secured to a first driven roller, a second end secured to a second driven roller, the belt extending from the first driven roller, around the first transverse edge of the platform plate, above an upper surface of the platform plate, around the second transverse edge of the platform plate, and to the second driven roller. The transfer device also has a first motor configured for driving the first driven roller, and a second motor configured for driving the second driven roller independent of the first driven roller. The transfer device also has a treatment system configured to apply a cleaning and/or disinfecting treatment to at least one of the transfer belt and the platform plate.

The transfer belt can make it possible to load an object onto the transfer platform and/or unload the object from the transfer platform without having to manually manipulate the object. At the same time, the transfer platform of the transfer device can support two-sided functionality, which can be useful when moving an object such as a patient from a first surface onto the transfer platform and then onto a second surface. This is a notable improvement over transfer platforms which do not support two-sided functionality.

In some implementations, the transfer belt is a first transfer belt and the transfer device also has a second transfer belt extending below a bottom surface of the platform plate on the first side of the device body, and a third transfer belt extending below a bottom surface of the platform plate on the second side of the device body. The second and third transfer belts can help avoid or mitigate friction between the first transfer belt and an upper surface holding or receiving the object.

In some implementations, the transfer device has a locking mechanism to selectively detach and attach the second transfer belt and the third transfer belt from and to the platform plate. The second and third transfer belts can selectively attach and detach in order to enable the platform plate and the first transfer belt to dynamically cross-over-center from the first side of the device body to the second side of the device body, and vice-versa, even while there is a patient or object on top of the platform plate. The second and third transfer belts can also be detached for example for cleaning or maintenance purposes.

Other aspects and features of the present disclosure will become apparent, to those ordinarily skilled in the art, upon review of the following description of the various embodiments of the disclosure.

BRIEF DESCRIPTION OF THE DRAWINGS

For a better understanding of the described embodiments and to show more clearly how they may be carried into effect, reference will now be made, by way of example, to the accompanying drawings in which.

DETAILED DESCRIPTION OF EMBODIMENTS

It should be understood at the outset that although illustrative implementations of one or more embodiments of the present disclosure are provided below, the disclosed systems and/or methods may be implemented using any number of techniques. The disclosure should in no way be limited to the illustrative implementations, drawings, and techniques illustrated below, including the exemplary designs and implementations illustrated and described herein, but may be modified within the scope of the appended claims along with their full scope of equivalents.

Overview of Transfer Device

The drawings illustrate example embodiments of a transfer device 100, which can be used to move a human body (or other object) from a first location to a second location and/or to re-position the human body (or other object) on a surface. An overview of the transfer device 100 is provided in this section with reference FIGS. 1 to 5. It is to be understood at the outset that the transfer device 100 is shown with very specific features for exemplary purposes only. Other implementations are possible and are within the scope of the disclosure.

Figure 1:
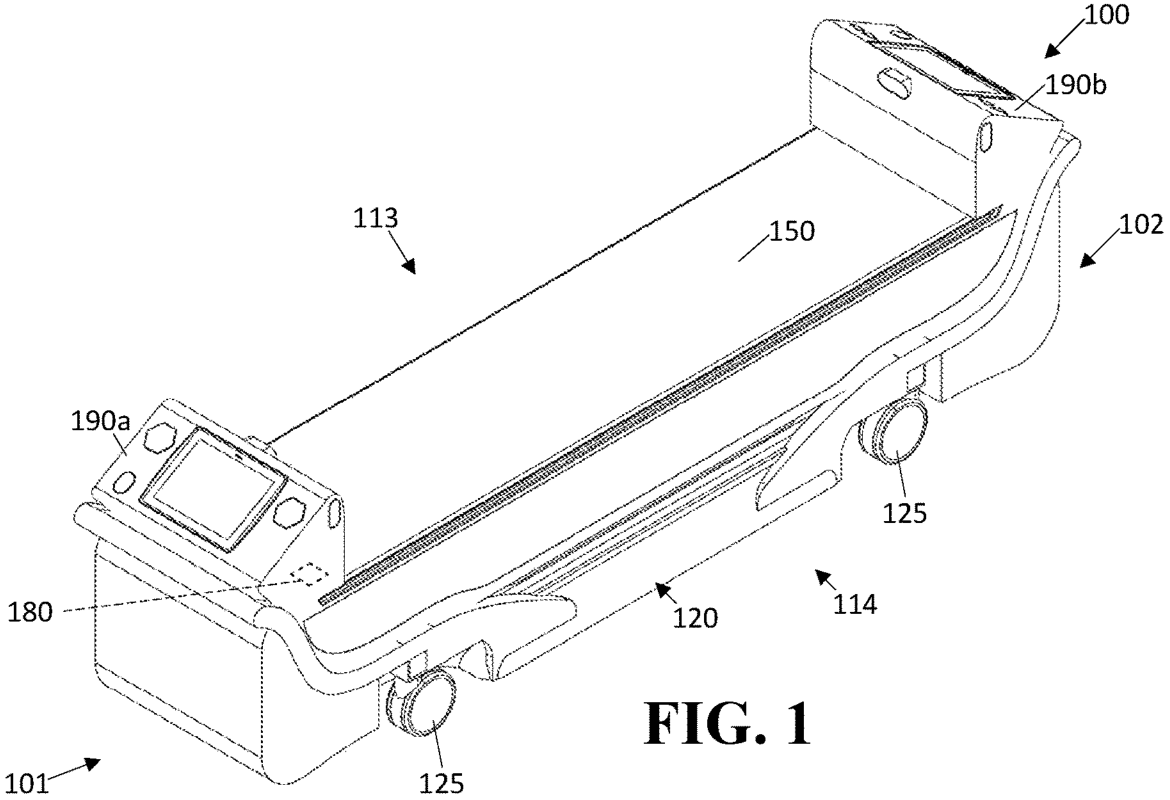
FIG. 1 is a perspective view of a transfer device, in accordance with an embodiment.
Figure 2:
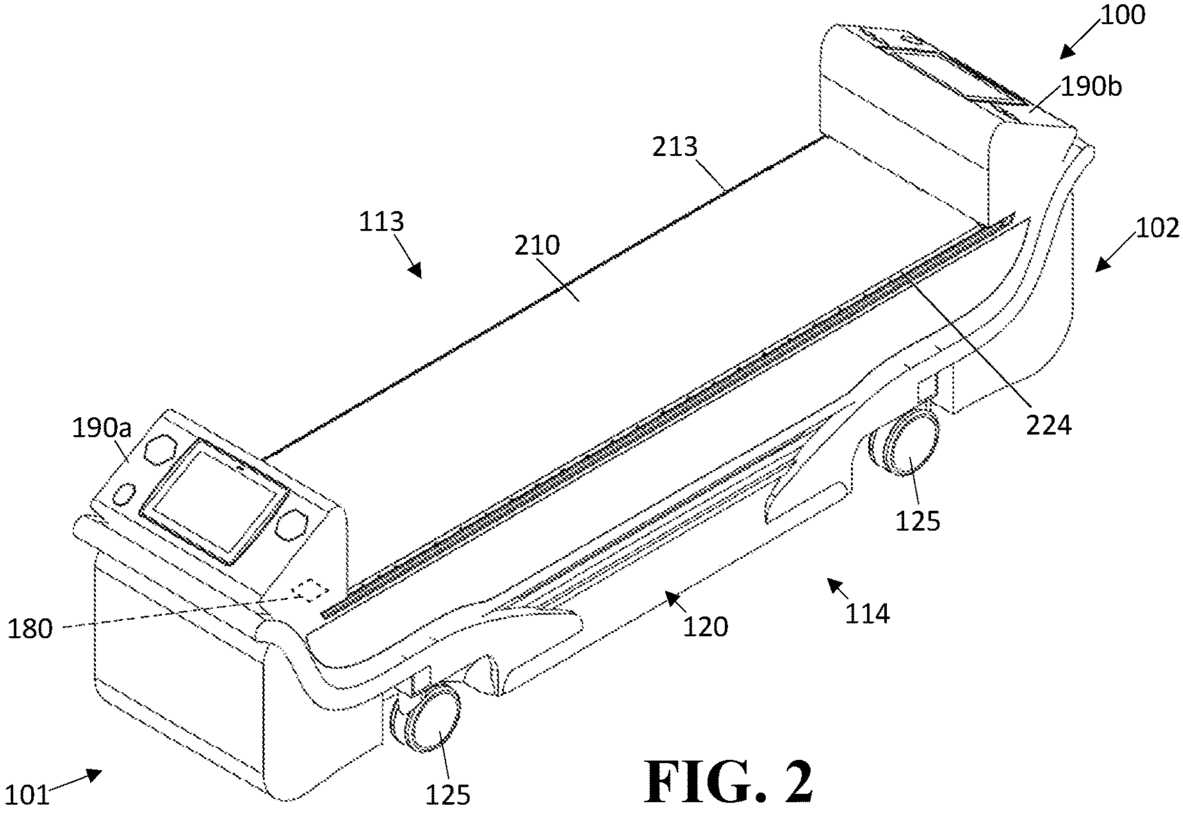
FIG. 2 is a perspective view of the transfer device of FIG. 1 with a transfer belt omitted for clarity.

With reference to FIGS. 1 and 2, the transfer device 100 has a device body having a first end 101, a second end 102, a first side 113, and a second side 114. The transfer device 100 also has a transfer platform including a platform plate 210 and a platform lateral actuator. In some implementations, the transfer device 100 has a transfer belt 150 covering the platform plate 210 as shown in FIG. 1. Note that the transfer belt 150 has been removed from FIG. 2 for clarity and to reveal the platform plate 210.

The platform lateral actuator is configured to selectively move the platform plate 210 laterally relative to the device body, such that the platform plate 210 can be moved between a plurality of positions including (i) a stowed position in which the platform plate 210 is retracted relative to the device body, (ii) a first extended position in which a first transverse edge 213 of the platform plate 210 is a leading edge that extends outward from the first side 113 of the device body, and (iii) a second extended position in which a second transverse edge 224 of the platform plate 210 is a leading edge that extends outward from the second side 114 of the device body.

Figure 3A:
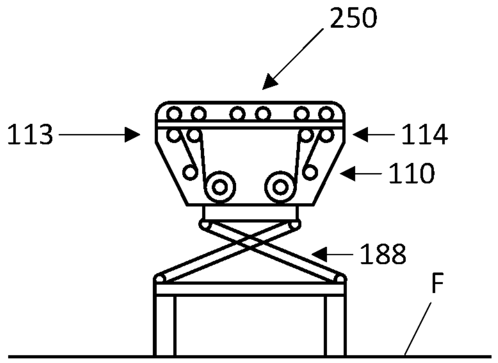
FIGS. 3A to 3C are schematics of the transfer device of FIG. 1 showing a retracted position, a first extended position, and a second extended position.
Figure 3B:
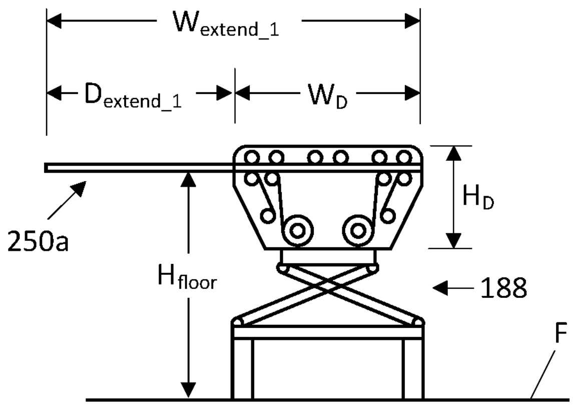
Figure 3C:
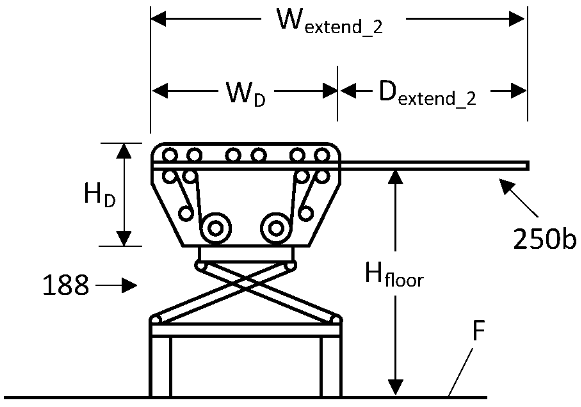
Figure 4:
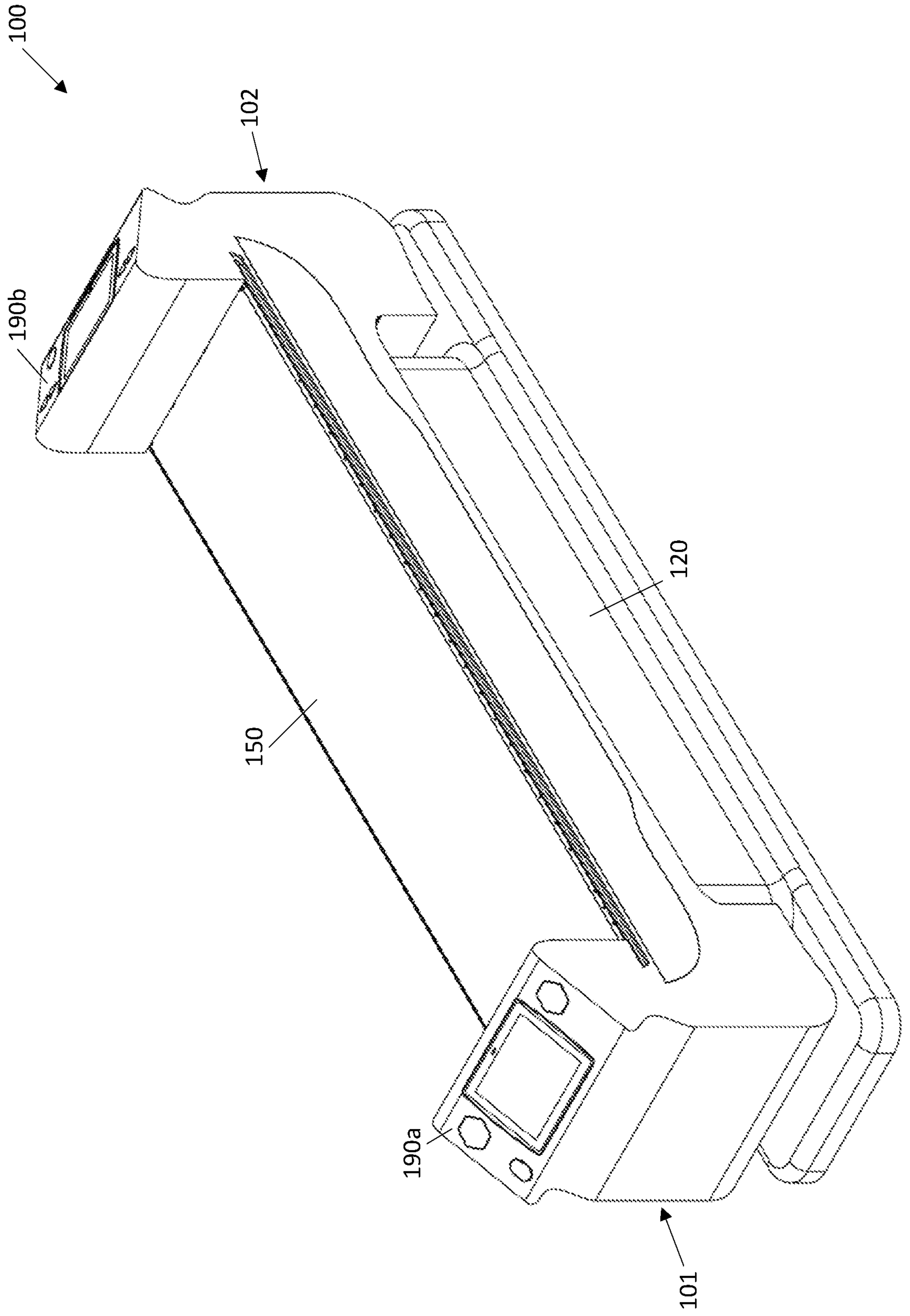
FIG. 4 is a perspective view of another transfer device having a fixed base.

With reference to FIGS. 3A to 3C, an example operation of the transfer device 100 is illustrated schematically, showing how a transfer platform 250 can be extended outward using the platform plate 210. In the position shown in FIG. 3A (which may be referred to as a stowed position or as a retracted position), the platform plate 210 is positioned centrally within the device body 110.

In the position shown in FIG. 3B, a transfer platform 250*a* has been extended out from the first side 113 of the device body 110. The transfer platform 250*a* may be extended out by the platform plate 210 being extended laterally outward by the platform lateral actuator.

In the position shown in FIG. 3C, an transfer platform 250*b* has been extended out from the second side 114 of the device body 110. In this example, the transfer platform 250*b* may be extended out by the platform plate 210 being extended laterally outward by the platform lateral actuator.

FIGS. 3A to 3C illustrate how the transfer platform 250 and 250*a-b* of the transfer device 100 can support two-sided functionality, because the platform plate 210 can be extended out from the first side 113 and the second side 114 of the device body 110. This two-sided functionality can be useful when moving an object such as a patient from a first surface onto the transfer platform and then onto a second surface. This is a notable improvement over transfer platforms which do not support two-sided functionality.

In some implementations, the transfer platform 250 and 250*a-b* is covered by the transfer belt 150, including when it is being extended outward from the device body 110 and retracted back towards the device body 110. The transfer belt can make it possible to load an object onto the transfer platform and/or unload the object from the transfer platform without having to manually manipulate the object.

In some implementations, the transfer belt 150 is driven using one or more actuators such that, when the transfer platform 250 and 250*a-b* is being extended outward from the device body 110 or retracted back towards the device body 110, a top surface of the transfer belt 150 is not moving and excess slack in the transfer belt 150 is avoided or mitigated. In some implementations, as described in further detail below, the transfer belt 150 has a first end secured to a first driven roller, a second end secured to a second driven roller, such that the belt extends from the first driven roller, around the first transverse edge of the platform plate 210, above an upper surface of the platform plate 210, around the second transverse edge of the platform plate 210, and to the second driven roller.

In some implementations, as described in further detail below, the transfer belt 150 is a first transfer belt, and the transfer device 100 also has a second transfer belt extending below a bottom surface of the platform plate 210 on the first side of the device body, and a third transfer belt extending below a bottom surface of the platform plate 210 on the second side of the device body. The second and third transfer belts can help avoid or mitigate friction between the first transfer belt and an upper surface holding or receiving the object.

In some implementations, the transfer device 100 has a locking mechanism to selectively detach and attach the second and third transfer belts from and to the platform plate 210, in order to enable the platform plate 210 and first transfer belt 150 to dynamically cross-over-center from the first side 113 of the device body 110 to the second side 114 of the device body 110, and vice-versa, even while there is a patient or object on top of the platform plate 210. The second and third transfer belts can also be detached for example for cleaning or maintenance purposes. Further example details of the locking mechanism are provided later with reference to FIGS. 22A to 22F and FIGS. 23A to 23G.

In some implementations, the transfer device 100 has a belt treatment system which can be used to clean or sterilize the first transfer belt 150, the second transfer belt and/or the third transfer belt. Further example details of the belt treatment system are provided below.

In some implementations, the transfer device 100 has a platform plate treatment system which can be used to clean or sterilize the platform plate 210 of the transfer device 100. Further example details of the platform plate treatment are provided below.

As shown in FIGS. 3A to 3C, the device body 110 has a width $W_D$ and a height $H_D$. The device body 110 can be supported above a floor service F by a distance $H_{floor}$. In some implementations, as shown in FIG. 3B, the transfer platform 250*a* may be extended by an extended or cantilevered distance $D_{extend\_1}$ from the first edge 113 of the device body 110, providing an overall platform width $W_{extend\_1}$. In some implementations, as shown in FIG. 3C, the transfer platform 250*b* may be extended by an extended or cantilevered distance $D_{extend\_2}$ from the second edge 114 of the device body 110, providing an overall platform width $W_{extend\_2}$.

In some implementations, as can be seen from FIGS. 3A to 3C, the extended distance $D_{extend\_1}$ of transfer platform 250*a* is approximately equal to the width $W_D$ of the device body 110. In some implementations, the transfer platform 250 can extend by about the width of the device body 110 (e.g. within 25% of that width). For example, if the width of the device body 110 is between $W_D$=400 mm to 1000 mm, then the transfer platform 250*a* can extend by a distance of between $D_{extend\_1}$=360 mm to 1250 mm, providing an overall platform width of about $W_{extend\_1}$=760 mm to 2250 mm. In some implementations, there are corresponding measurements for the transfer platform 250*b* in the other direction.

In another implementation, the transfer device 100 has a nested drawer system and telescoping actuator (not shown) enabling further extension of the transfer platform 250 in the first and second extended positions, such that the platform plate 210 extends outward by a distance that is greater than the width of the device body by 10% to 110%. For example, if the width of the device body 110 is between $W_D$=400 mm to 1250 mm, the transfer platform 250*a* can extend by a distance of between $D_{extend\_1}$=440 mm to 1600 mm, providing an overall platform width of about $W_{extend\_1}$=840 mm to 2850 mm. In some implementations, there are corresponding measurements for the transfer platform 250*b* in the other direction.

Enabling the transfer platform 250*a-b* to extend by more than the width of the device body 110 may have one or more advantages. For example, this may facilitate maneuvering the transfer device 100 through tight hallways, and/or may reduce the storage footprint of the transfer device when the transfer platform is retracted. This is made possible by the nested drawer system and telescoping actuator as noted above.

A relatively narrow width $W_D$ can advantageously facilitate maneuvering the transfer device 100 and/or reduce its storage footprint. However, in some cases it may be desirable for the transfer device 100 to have a supported (i.e. non-cantilevered) surface that has a relatively wider width Wo. For example, the device body 110 can have a wider non-cantilevered support surface to provide increased comfort and/or safety when transporting a patient between locations by moving the transfer device 100 across a floor surface.

In some implementations, the transfer device 100 has a support structure 188 configurable to adjust a height of the device body 110 above the floor surface F and/or an angle of the device body 110. In some implementations, the support structure 188 can adjust height and tilt of the device body 110 in both the long and short axis. In some implementations, the support structure 188 has actuators coupled to a transfer device controller for controlling the height and/or the tilt of the device body 110. This can allow for changes in an angle of approach of the transfer platform in advance of or during transfer in order to reduce reactionary forces on the device, reduce the pressure applied to the patient (or object) being transferred or allow for medically advantageous positions when a patient is on the transfer platform such as Trendelenburg or reverse Trendelenburg position. The actuation of these support actuators may be controlled by a main transfer device controller or separately by its own controller and operate in parallel through electronic communication with the transfer controller.

Referring back to FIGS. 1 and 2, in some implementations, the transfer device 100 has a base 120 that includes wheels 125 for assisting in translating the transfer device 100 across a floor surface. Some or all of the wheels 125 can be driven by a motor, such that the transfer device 100 is able to transport itself across the floor surface. However, it will be appreciated that the wheels 125 are optional. In other implementations, the transfer device 100 is not configured for easy mobility across a floor service. For example, with reference to FIG. 4, the transfer device 100 can have a fixed base 120 with no wheels 125. Such implementations may be advantageous if the transfer device 100 is not intended to be moved during normal operation. For example, the transfer device 100 may be in a fixed position adjacent a bed of a CT or MRI machine.

In some implementations, the transfer device 100 has at least one control panel coupled to the transfer device controller to allow a user to operate the transfer device 100. For example, with reference to FIGS. 1 and 2, the transfer device 100 has two control panels 190*a-b*, including one control panel 190*a* at the first end 101 of the device body 110, and another control panel 190*b* at the second end 102 of transfer device 100. It will be appreciated that, in other implementations, there may be only one control panel. Alternatively, or additionally, the transfer device 100 may be configured to be controlled from a remote device (e.g. pendant or tethered remote control, a mobile computing device, such as a tablet or laptop computer, or a control panel positioned elsewhere in a room in which the transfer device is positioned, or in an adjacent room), in which case the transfer device 100 could have no control panel.

In some implementations, the transfer device 100 has a transfer device controller 180, which can control one or more actuators (e.g. motors) such as the platform lateral actuator of the platform plate 210 to extended or retract the transfer platform 250 and 250*a-b*. In some implementations, the first driven roller and the second driven roller for the transfer belt 150 are operably coupled to the transfer device controller 180, and the transfer device controller 180 is configured to selectively actuate the first driven roller and the second driven roller concurrently or separately from each other. In this way, the transfer device controller 180 can control slack of the transfer belt 150. The transfer device controller 180 can also control the belt treatment system and/or the platform plate treatment system.

In some implementations, the transfer device controller 180 is coupled to one or more sensors of the transfer device 100, and utilizes data from the sensors when operating the transfer device 100. In some implementations, the controller synchronizes and directly controls the transfer device 100 with its subsystems, provides feedback to the user in regards to a state of the transfer device 100, and uses the state it is monitoring in order to provide safe operation (e.g. shutting the system down automatically if the transfer device 100 is operating in an unsafe manner).

In some implementations, the transfer device controller 180 is a single controller (e.g. single microcontroller) configured to handle all controllable subsystems of the transfer device 100. In other implementations, the transfer device controller 180 includes multiple controllers (e.g. separate microcontrollers) for handling the controllable subsystems of the transfer device 100. Thus, the term "transfer device controller" covers one or more controllers (e.g. one or more microcontrollers). The purpose for utilizing more than one controller may be to reduce sensor transmission lengths, increase redundancy and/or locate the controllers advantageously, physically within the transfer device 100 to reduce latency. Multiple controllers may also be utilized due to practical limitations of current state of the art controllers (e.g. number of available General Purpose Input Outputs). For example, a first controller may be placed on the first end 101 and a second controller may be placed the second end 102 to capture signals from sensors mounted on each end independently.

There are many possibilities for the controllable subsystems of the transfer device 100. As described herein, some possibilities for the controllable subsystems can include platform lateral actuator(s), driven roller(s) for transfer belt(s), a belt treatment system, and/or a platform plate treatment system. Additional or other controllable subsystems may be possible.

Figure 5:
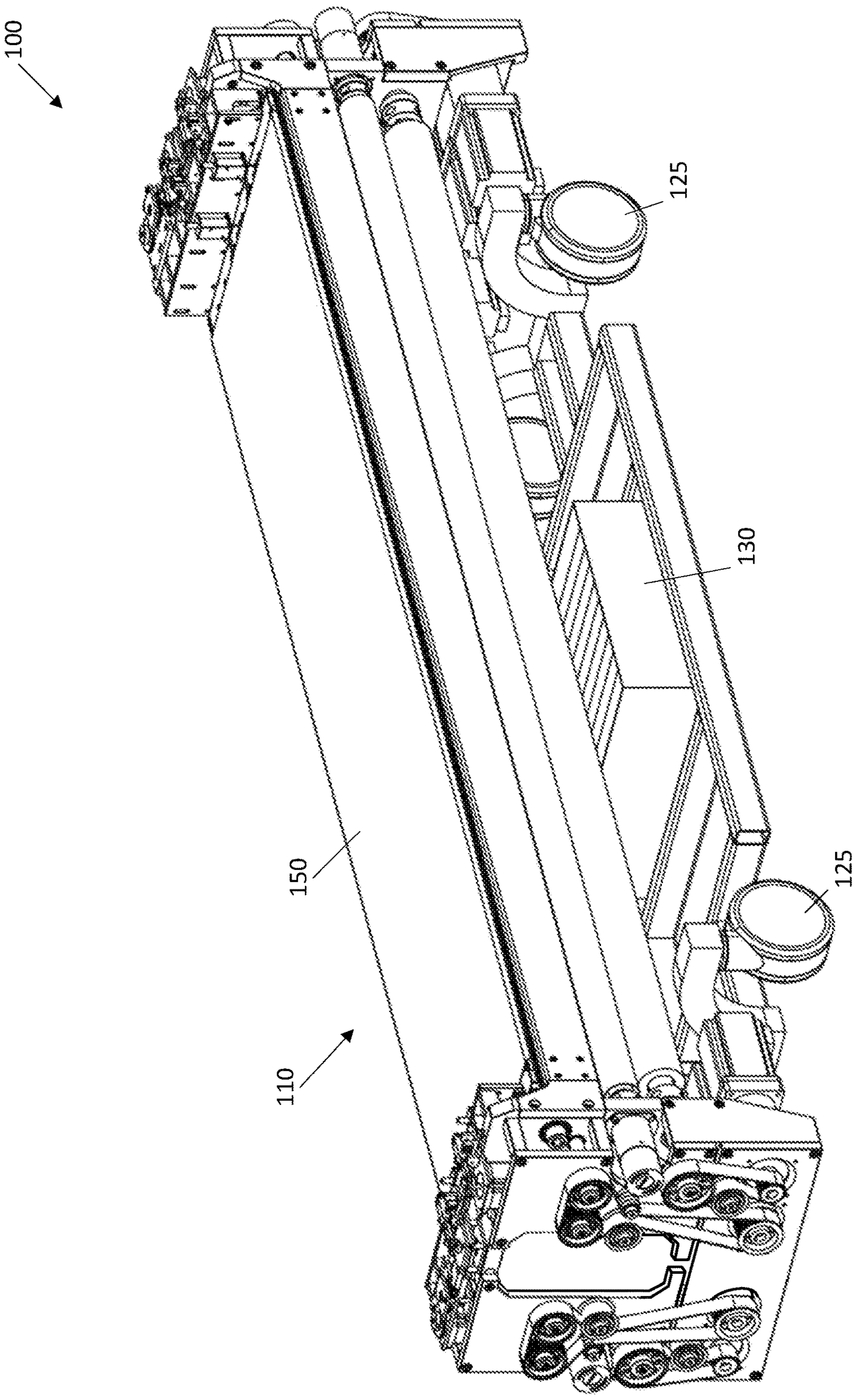
FIG. 5 is a perspective view of the transfer device of FIG. 1 with housing portions omitted for clarity.

In some implementations, the one or more actuators controlled by the transfer device controller 180 are powered via a battery, which can help to enable the transfer device 100 to be portable. For example, with reference to FIG. 5, shown is the transfer device 100 with the housing and control panels 190*a-b* removed for clarity and to reveal a battery pack 130 that can supply power to the transfer device controller 180, actuators (e.g. motors), etc. of the transfer device 100. Alternatively, a battery pack may not be provided, and transfer device 100 may be connected to an external source of electrical power.

The examples described herein generally focus on the transfer device 100 having a transfer device controller 180, which is configured to control the transfer platform, and optionally provides additional functionality as described herein. However, in another embodiment, the transfer device 100 can be implemented without any transfer device controller 180. For instance, the transfer device 100 could be entirely analogue and designed to function without a device controller.

Transferring a Human Body

Example operation of the transfer device 100 in transferring a human body from a first surface to a second surface will now be described with reference to FIGS. 6A to 6G. The operation will be described in connection with the transfer device 100 transferring a human body 10 from a gurney 20 to a bed 30 (e.g. a bed associated with a medical imaging device, such as CT or MRI scanner). However, it is to be understood that the transfer device 100 may be used to transfer a human body (or other object) off of and on to any raised surface in substantially the same manner.

Figure 6A:
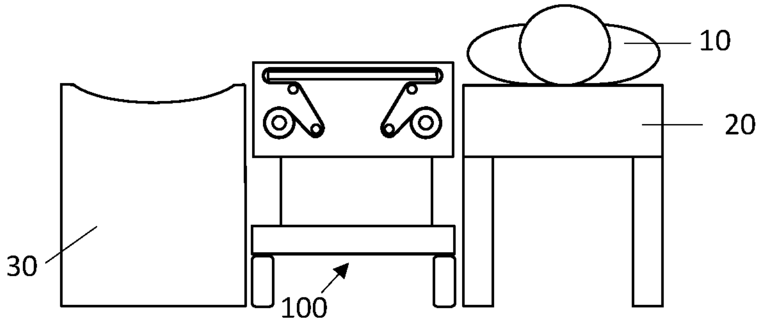
FIGS. 6A to 6G are a series of schematics illustrating the transfer device of FIG. 1 being used to transfer a human from a gurney onto a bed of a medical imaging scanner.

The transfer device 100 is positioned between the gurney 20 with the human body to be transferred and the bed 30, e.g. in the position shown in FIG. 6A, with the leading edge of the platform plate at a similar elevation to the surface of the gurney 20 on which the human body 10 is supported. For example, the transfer platform 100 may be supported by a wheeled base 120 as shown in FIGS. 1 and 2.

Figure 6B:
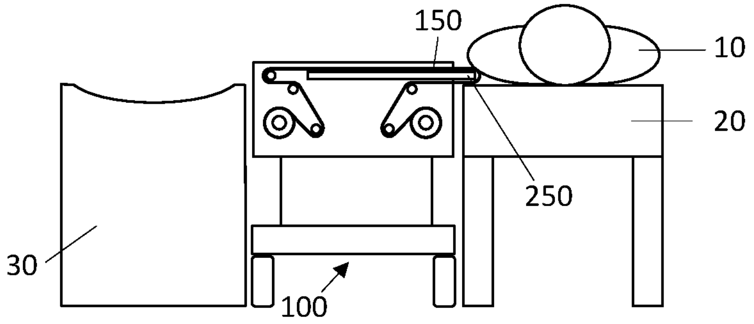

Referring to FIG. 6B, platform lateral actuators (e.g. platform drive pinions 382 as described later, not shown in FIGS. 6A-G) can be used to extend the leading edge of the transfer platform laterally outwardly from a side of the transfer device 100. The transfer platform 250 may be extended until at least a portion of the transfer platform 250 is positioned below the human body 10 (and preferably completely between the surface of the gurney 20 and the human body 10), with a portion of the transfer belt 150 positioned between the transfer platform 250 and the human body 10.

Figure 6C:
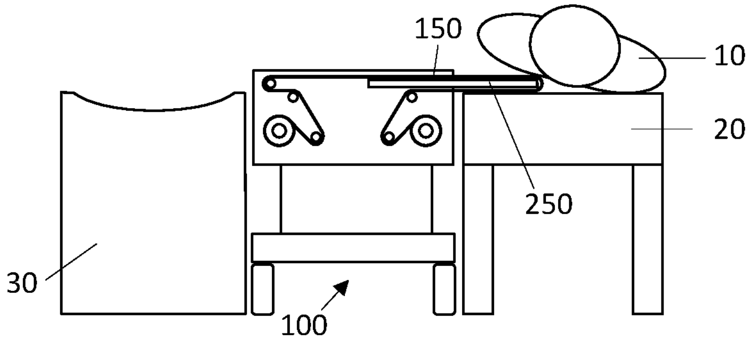
Figure 6D:
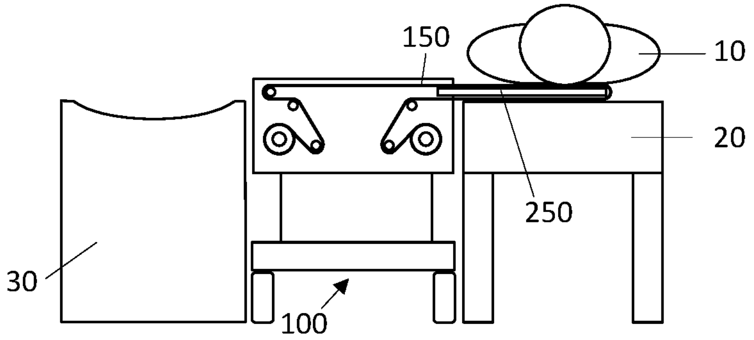

In some implementations, the motion of transfer platform 250 and/or the transfer belt 150 is controlled to provide limited (or zero) relative motion between an upper surface of transfer platform 250 (i.e. the transfer belt 150) and the human body 10 during some or all of the transfer. In this way, the transfer platform 250 can be extended outward and under the human body 10 as shown in FIGS. 6B to 6D without having to lift the human body 10 or roll the human body 10 onto the transfer platform 250.

Optionally, a lower surface of a guard layer (e.g. guard layer 155 as described later, not shown in FIGS. 6A to 6G) may be in contact with the surface of the gurney 20 supporting the human body 10 before and during the transfer. Also, while not illustrated, it will be appreciated that the supporting surface 20 may be displaced and/or compressed by the transfer platform 250, e.g. to reduce force on the human body 10, particularly when the transfer platform 250 is being extended outward and under the human body 10 as shown in FIGS. 6B to 6D.

In some implementations, to enable limited relative motion between the upper surface of transfer platform 250 (i.e. the transfer belt 150) and the human body 10 while the transfer platform 250 is being extended outward from the transfer device 100 (i.e. FIGS. 6B to 6D), there is relative motion between the transfer belt 150 and the surface of the gurney 20. For instance, while the transfer platform 250 is being extended outward from the transfer device 100, the transfer belt 150 is pushing outward on the surface of the gurney 20. To reduce or mitigate friction between the transfer belt 150 and the surface of the gurney 20, the surface of the gurney 20 can include a low friction bed sheet to enable the movement of the transfer belt 150. Alternatively, to reduce friction due to the relative motion, the transfer belt 150 may be made of a low friction material designed to perform such patient moving operations. Some examples of the aforementioned low friction belt material may be silicone or Polytetrafluoroethylene (PTFE) coated nylon or polyester fabrics.

Preferably, driven rollers (e.g. driven rollers 160*a* and 160*b* as described later, not shown in FIGS. 6A to 6G) may be controlled to take-up slack in the transfer belt 150 during the extension and/or retraction of the transfer platform 250. For example, tension in transfer belt 150 may be controlled throughout the transfer process by monitoring one or more of the following exemplary sensors: current from motor drivers, compression distance of a tensioner (e.g. tensioner 900 as described later, not shown in FIGS. 6A to 6G), strain sensors (not shown) embedded into the transfer belt 150, and/or other suitable sensors.

Figure 6E:
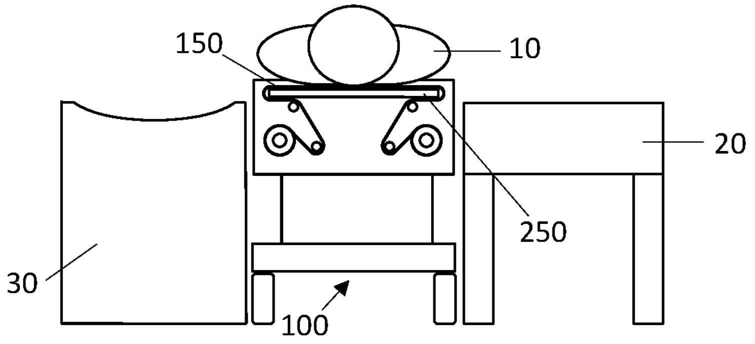

Referring to FIGS. 6D and 6E, the driven rollers are then actuated to convey the human body 10 along upper surfaces of the transfer platform 250. For example, this may be achieved by 'winding' one driven roller while concurrently 'unwinding' the other driven roller to advance the upper surface of the transfer belt 150 towards the opposite side of the transfer device 100 in an actively controlled manner.

While the human body 10 is being moved from the gurney 20 towards the transfer device 100 (FIGS. 6D to 6E), if the transfer platform 250 is not being retracted towards the transfer device 100, then the transfer belt 150 continues to push outward on the surface of the gurney 20. Again, to reduce or mitigate friction between the transfer belt 150 and the surface of the gurney 20, the surface of the gurney 20 can include a low friction bed sheet to enable the movement of the transfer belt 150. Again, alternatively the transfer belt 150 may be comprised of a low friction textile. Although not depicted, in another implementation, the transfer platform 250 is retracted towards the transfer device 100 at the same time as the human body 10 is being moved from the gurney 20 towards the transfer device 100.

Figure 6F:
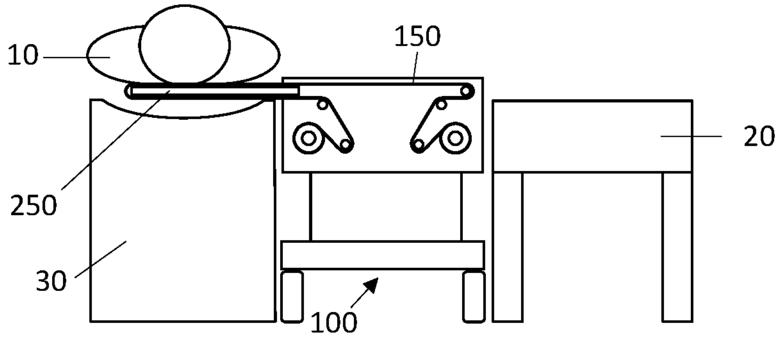

Referring to FIG. 6F, the human body 10 may then be transferred to the bed 30. For example, transfer device 100 may be controlled to laterally shift transfer platform 250 to a position overlying bed 30 while controlling transfer belt 150 to maintain the human body 10 above the transfer device 100, and then transfer belt 150 may be controlled to advance patient towards the bed 30. Alternatively, the transfer device 100 may be controlled to laterally shift the transfer platform 250 to a position overlying bed 30 while concurrently controlling transfer belt 150 to maintain the human body 10 above the advancing end of the transfer platform, until the human body 10 and the transfer platform 250 overlie the bed 30.

Figure 6G:
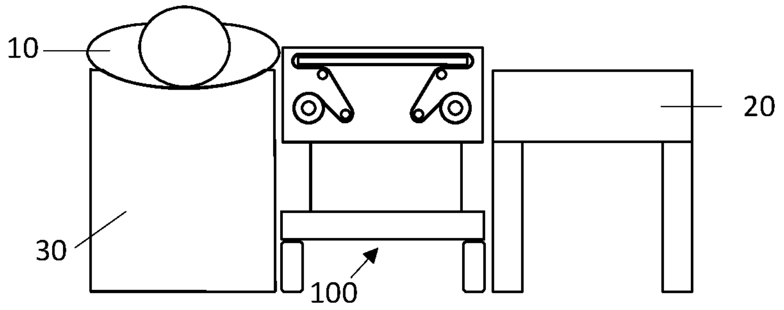
Figure 7A:
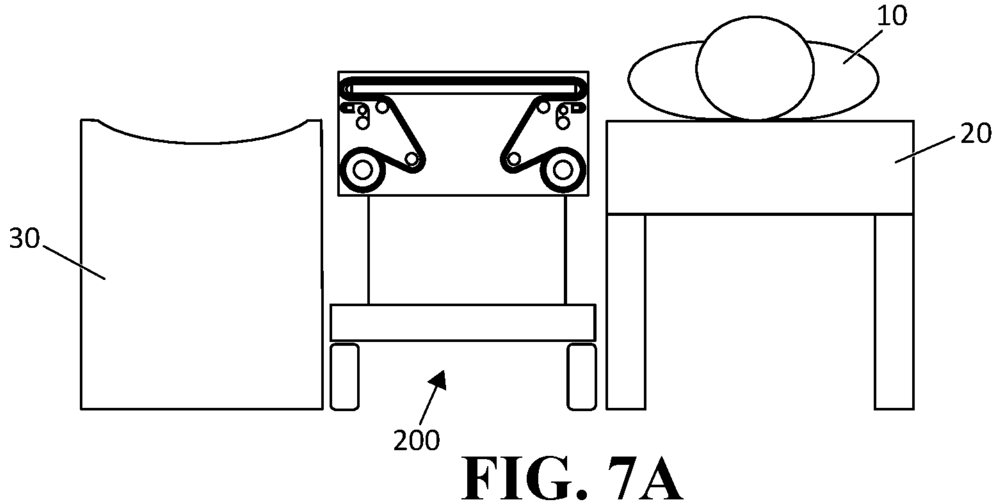
FIGS. 7A to 7E are a series of schematic illustrating another transfer device being used to transfer a human.
Figure 7B:
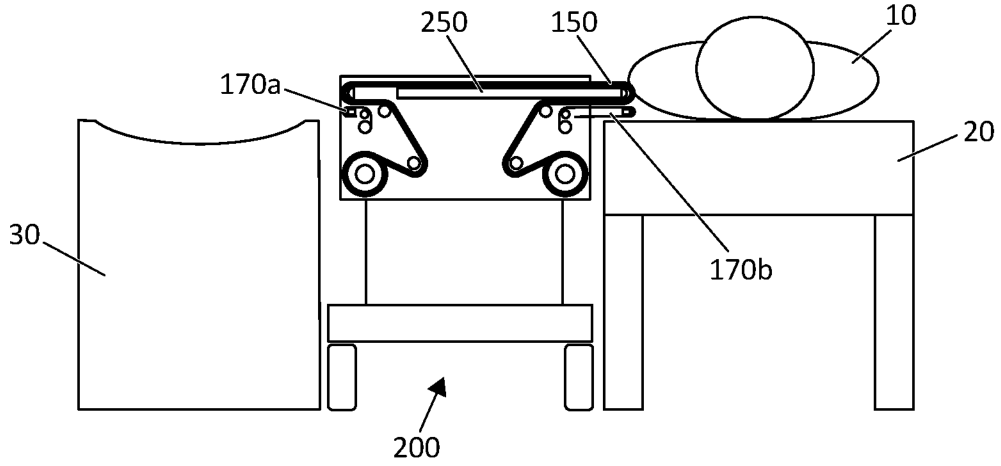
Figure 7C:
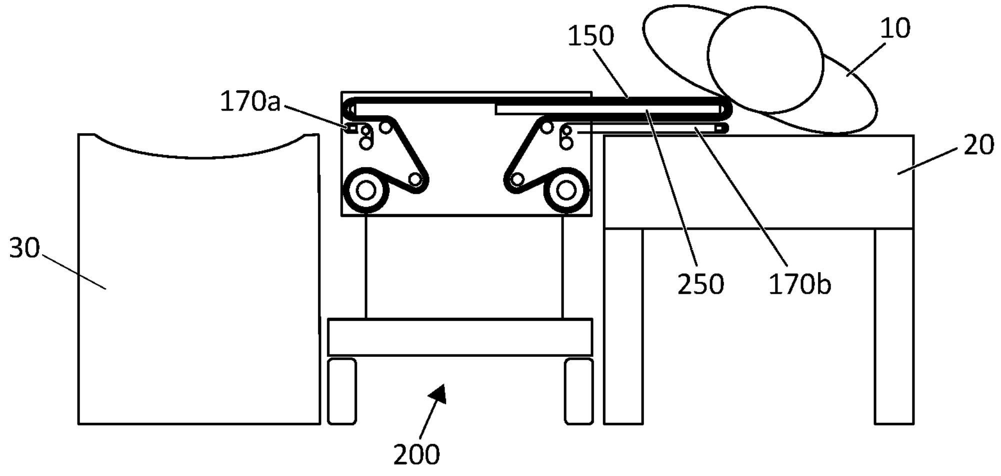
Figure 7D:
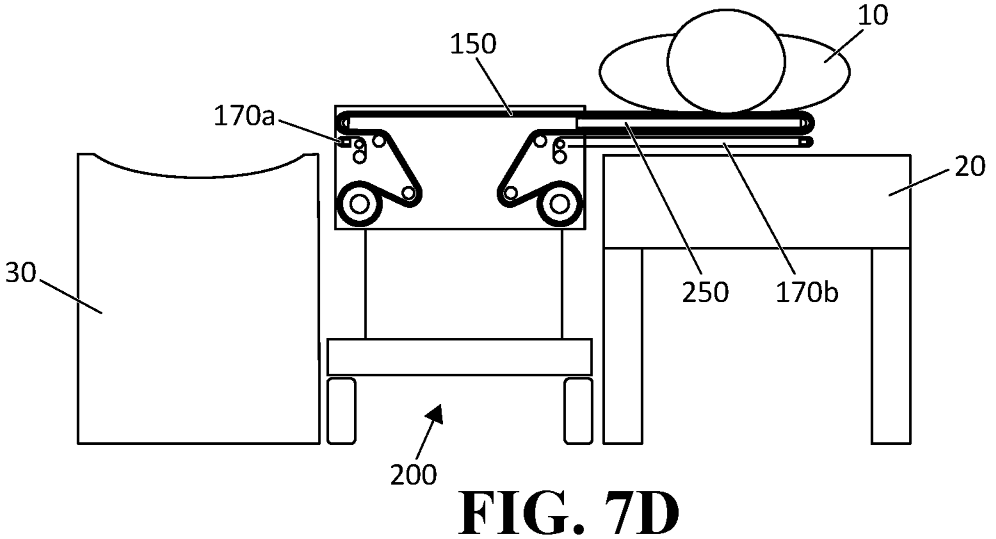
Figure 7E:
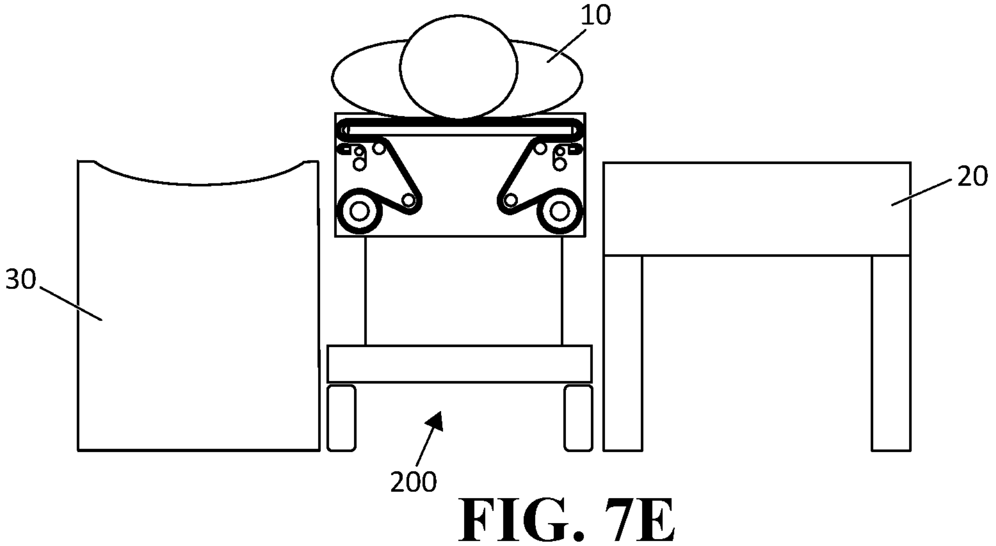

With reference to FIG. 6G, following the platform lateral actuators (e.g. platform drive pinions 382) may be used to retract the transfer platform 250 from underneath the human body 10. As illustrated, the transfer platform 250 may be shifted laterally until clear of the patient, at which point the transfer platform 250 may be in a stowed position within the device body 110.

It will be appreciated that, in use, at least some, preferably most, and more preferably substantially all of the transfer platform 250 is supported vertically by a surface onto which an object is to be transferred using the transfer platform 250, or a surface from which an object to be transferred is resting. In the illustrated example, the transfer platform 250 receives vertical support from the gurney 20 (FIGS. 6B-6E) and the bed 30 (FIG. 6F).

To transfer the patent 10 from the bed 30 to the gurney 20, the process illustrated in FIGS. 6A to 6G may be performed in reverse order.

As noted above, there can be friction between the transfer belt 150 and the surface of the gurney 20. While low friction bed sheets can reduce or mitigate such friction, other implementations are possible in which such friction can be largely avoided, because contact between the transfer belt 150 and the surface of the gurney 20 can be mitigated or avoided completely. For example, in other implementations, the transfer device 100 has a second transfer belt (not shown) extending below a bottom surface of the transfer platform 250 when the transfer platform 250 is extended outward, such that the second transfer belt provides limited or zero relative motion between the bottom surface of the transfer platform 250 and the surface of the gurney 20. Such an implementation is briefly described below with reference to FIGS. 7A to 7E.

With reference to FIGS. 7A to 7E, shown is another transfer device 200 transferring the human body 10 from the gurney 20 to the bed 30. The transfer device 200 of FIGS. 7A to 7E is similar to the transfer device 100 of FIGS. 6A to 6G, but includes lower guard belts 170*a-b*, including a second transfer belt 170*a* shown on the left side and a third transfer belt 170*b* shown on the right side, in addition to the first transfer belt 150 on top. When the transfer platform 250 is being extended out the towards and under the human body 10 (FIGS. 7B to 7D), the third transfer belt 170*b* provides limited or zero relative motion between the bottom surface of the transfer platform 250 and the surface of the gurney 20. Likewise, when the human body 10 is moved towards and on top of the transfer device 100 (FIG. 7E), the third transfer belt 170*b* provides limited or zero relative motion between the bottom surface of the transfer platform 250 and the surface of the gurney 20. The second transfer belt 170*a* operates substantially in the same way as the third transfer belt 170*b* but on the other side of the transfer device 200.

Therefore, FIGS. 7A to 7E demonstrate the operation of the transfer device 200 where the lower guard belts 170*a-b* have been routed in such a way that extension of the platform also draws out lower guard material from within the middle of the platform to create a lower no-shear surface simultaneously along with the upper surface. The first transfer belt 150 interacts with the patient at rest and the lower guard belts 170*a-b* interact with the patient's support surface. Each transfer belt 150 and 170*a-b* is operatively terminated such that when the transfer platform extends, the transfer belts 150 and 170*a-b* are drawn out from the centra cavity of the platform only, thereby unrolling under the patient and creating zero shear or relative velocity to the support surface or patient at rest. One or more of the transfer belts 150 and 170*a-b* may be comprised of a low friction material in order to reduce forces on the object being transferred, relative friction between the transfer belt 150 and the lower guard belts 170*a-b*, in addition to reducing reaction forces back to the transfer device 100 due to friction occurring during the act of transfer.

While the embodiments disclosed herein are described specifically in relation to and in use with transferring a human body (e.g. an individual with reduced, limited, or no mobility, an able bodied individual, an unconscious individual, an incapacitated individual, etc.), it will be appreciated that the embodiments disclosed herein may additionally or alternatively be used to transfer other objects, such as those that may be bulky, cumbersome, delicate, and/or difficult to grasp and move. For example, the embodiments disclosed herein may be suited and/or adapted for use to transfer livestock or domestic animals, undomesticated animals (e.g. in a zoo or wildlife care facility), human corpses (e.g. in a funeral home of a mortuary), inanimate objects (e.g. in courier, cargo, and/or logistical operations), and the like.

Example Implementation Details

Example implementation details of the transfer device 100 are provided in this section with reference to FIGS. 8 to 21D. It is to be understood at the outset that the transfer device 100 is shown in the Figures with very specific features for exemplary purposes only. Other implementations are possible and are within the scope of the disclosure.

Figure 8:
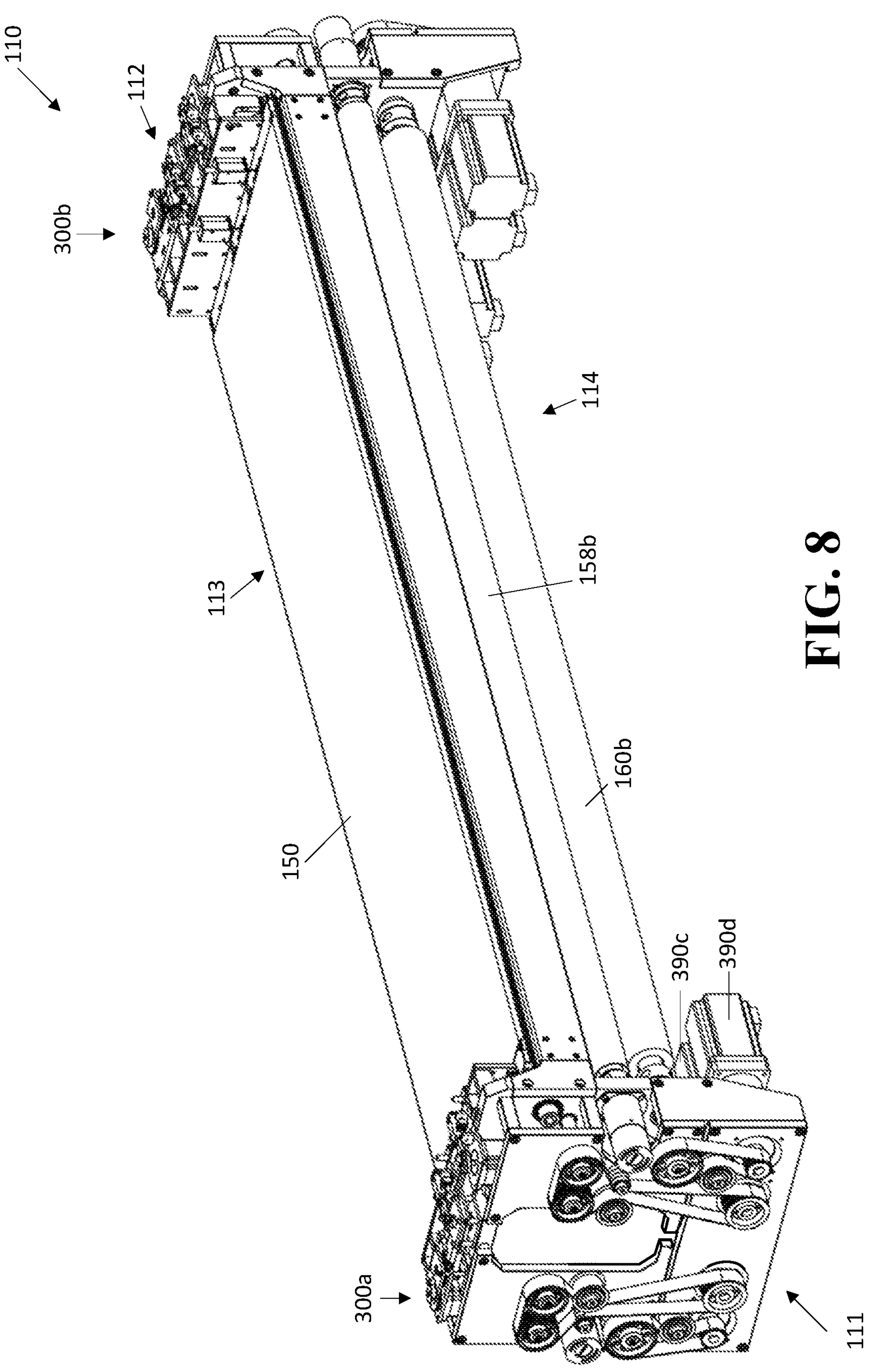
FIG. 8 is a perspective view of a transfer belt path of the transfer device of FIG. 1.

With reference to FIG. 8, the transfer device 100 includes a first end drive assembly 300*a* on a first end 111 corresponding to the first end 101 shown in FIGS. 1 and 2, and a second end drive assembly 300*b* on a second end 112 corresponding to the second end 102 shown in FIGS. 1 and 2. These end drive assemblies 300*a-b* are connected to each other by lateral support members, such that the end drive assemblies 300*a-b* are on opposite ends of the transfer device 100.

Figure 9:
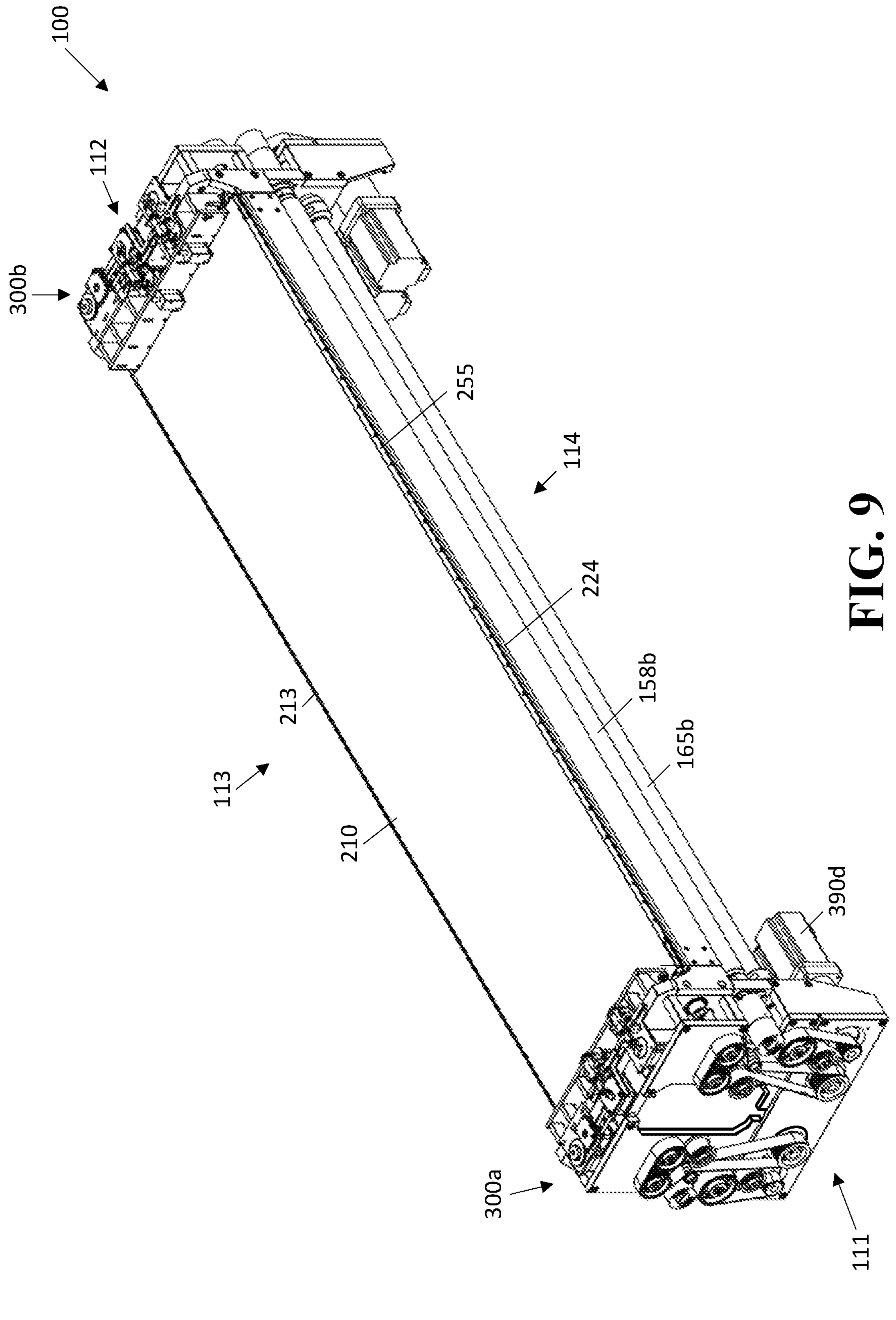
FIG. 9 is a perspective view of the transfer device of FIG. 8, with the transfer belt omitted for clarity.
Figure 10:
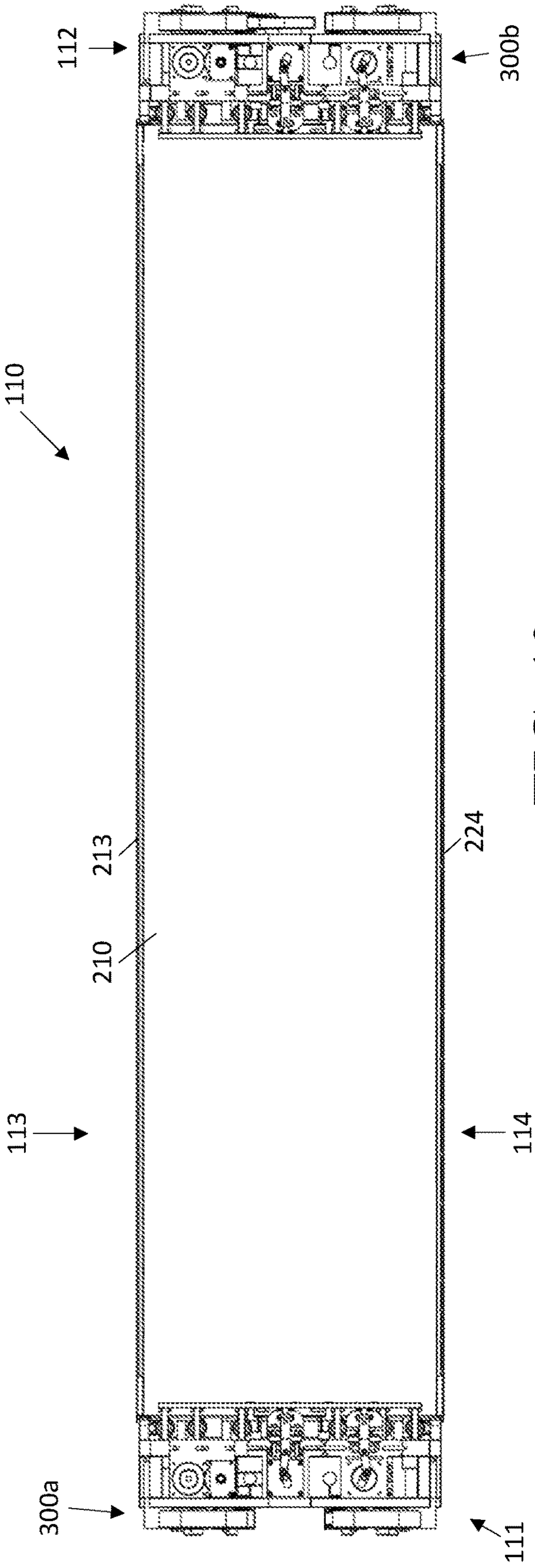
FIGS. 10 and 11 are top and side views of the transfer device of FIG. 9.
Figure 11:
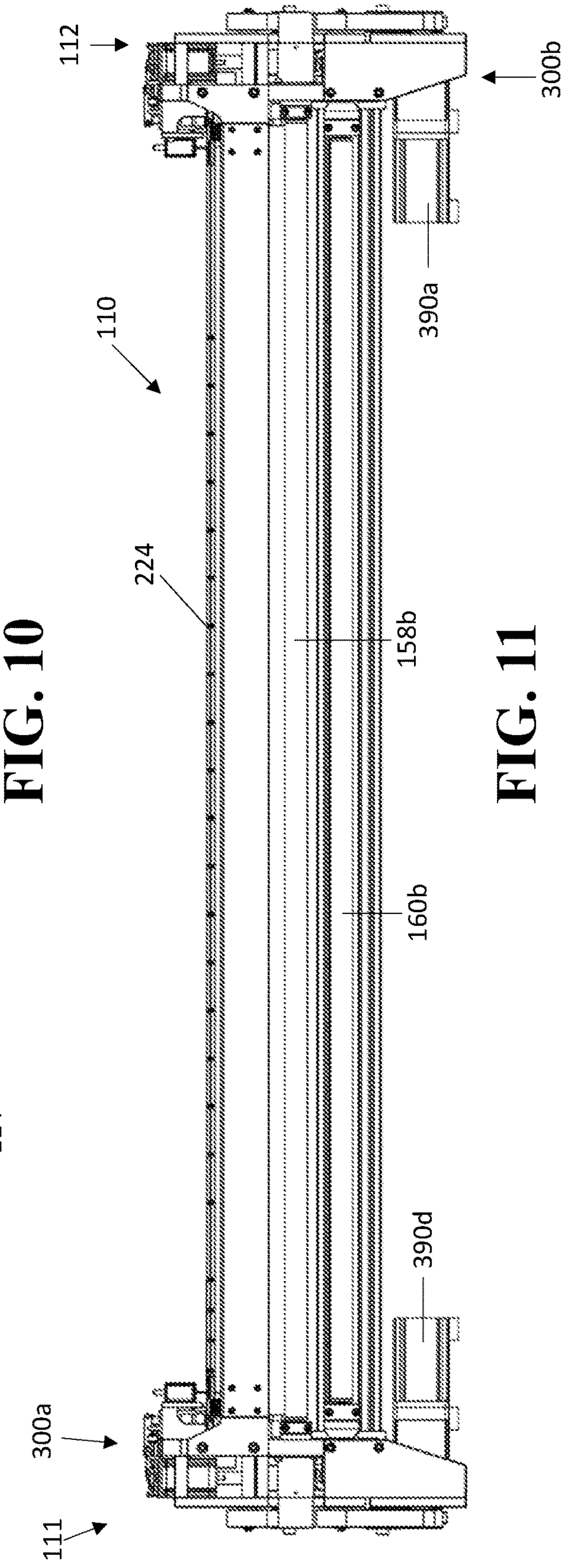

FIG. 9 shows the transfer device 100 without the transfer belt 150 thereby revealing the platform plate 210. FIGS. 10 and 11 are top and side views of the transfer device of FIG. 9. The end drive assemblies 300*a-b* are shown.

Figure 12A:
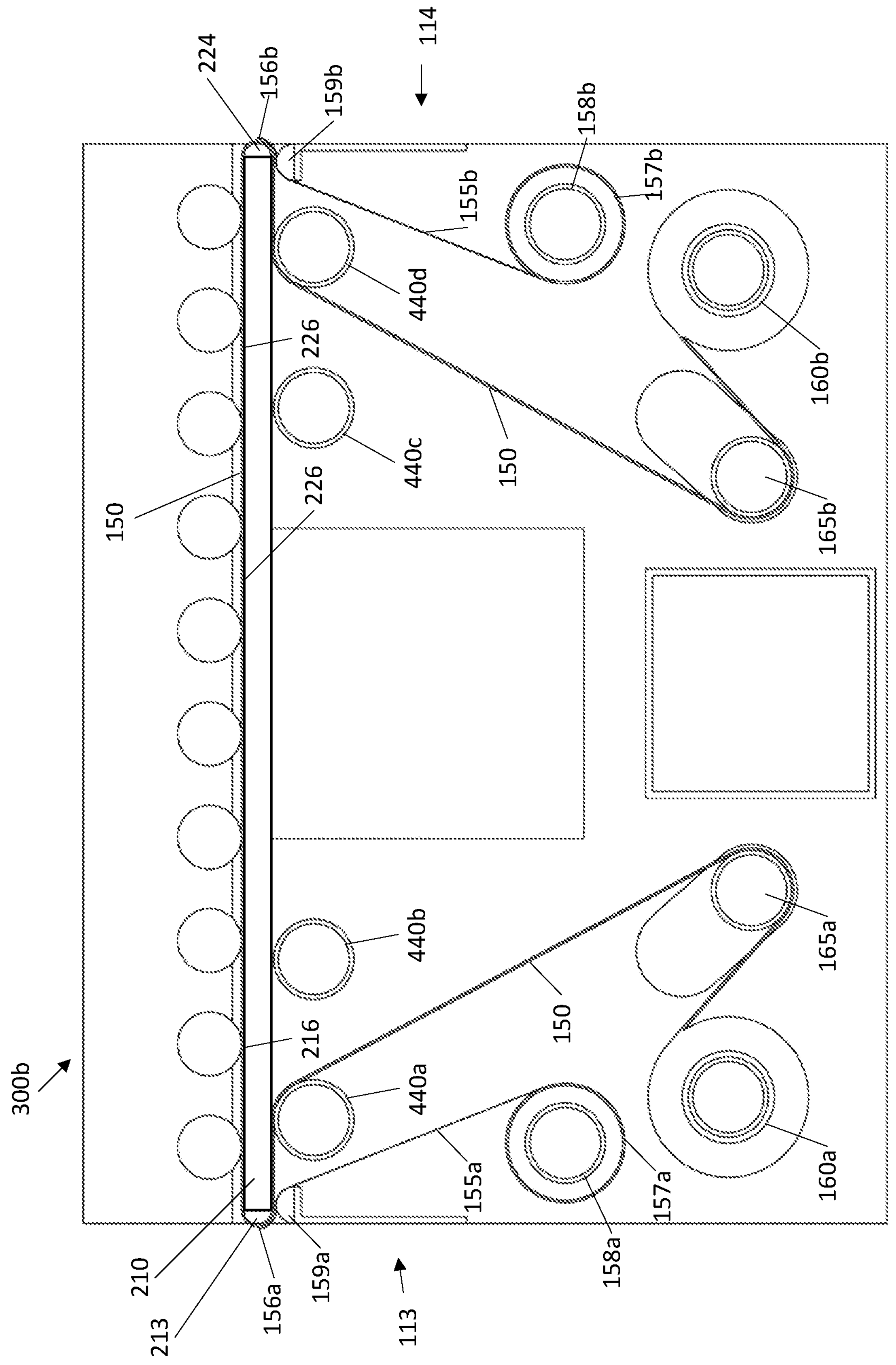
FIG. 12A is a schematic view of a transfer belt path of the transfer device of FIG. 1.

With reference to FIGS. 12A, details of the second end drive assembly 300*b* can be seen. In some implementations, the transfer belt 150 has a fixed length, and a first end of the transfer belt 150 is secured to a first driven roller 160*a*, and a second end of the transfer belt 150 is secured to a second driven roller 160*b*. Accordingly, the transfer belt 150 may be characterized as a discontinuous belt 150.

Utilizing a discontinuous transfer belt 150 may have one or more advantages. For example, this may facilitate the removal and/or replacement of the transfer belt 150 (e.g. by removing a driven roller with the transfer belt attached). This may result in the transfer device 100 being relatively easy to clean and/or maintain, which may result in reduced downtime. This may be of particular importance in use cases where cross-contamination is of concern (e.g. in hospitals, care homes, etc.).

Additionally, or alternatively, using a discontinuous belt with driven rollers on both ends may also have a mechanical advantage, in that the transfer belt's tension can be controlled from both ends of the belt. For example, this may assist in providing a desired tension level, and/or a desired level of 'slack' (or a lack thereof) in transfer belt 150.

As shown schematically in FIG. 12A, the transfer belt 150 extends from the first driven roller 160*a* and passes around a tensioner 165*a*. From there, the transfer belt 150 extends around a roller 440*a*, the first transverse edge 213 of the platform plate 210, along the upper surface 216 of the platform plate 210, and around the second transverse edge 224 of the platform plate 210. The transfer belt 150 then passes around a roller 440*d*, a tensioner 165*b*, and terminates at the second driven roller 160*b*.

In the illustrated example, the transfer belt 150 is guided around two passive (i.e. non-driven) rollers 165*a* and 165*b* to maintain tension and to avoid potentially interfering interactions with other components located within the housing (e.g. control systems, motors and motor drivers, gears, and the like). It will be appreciated that fewer, more, or no tensioners 165*a* and 165*b* may be provided in alternative implementations.

Figure 13:
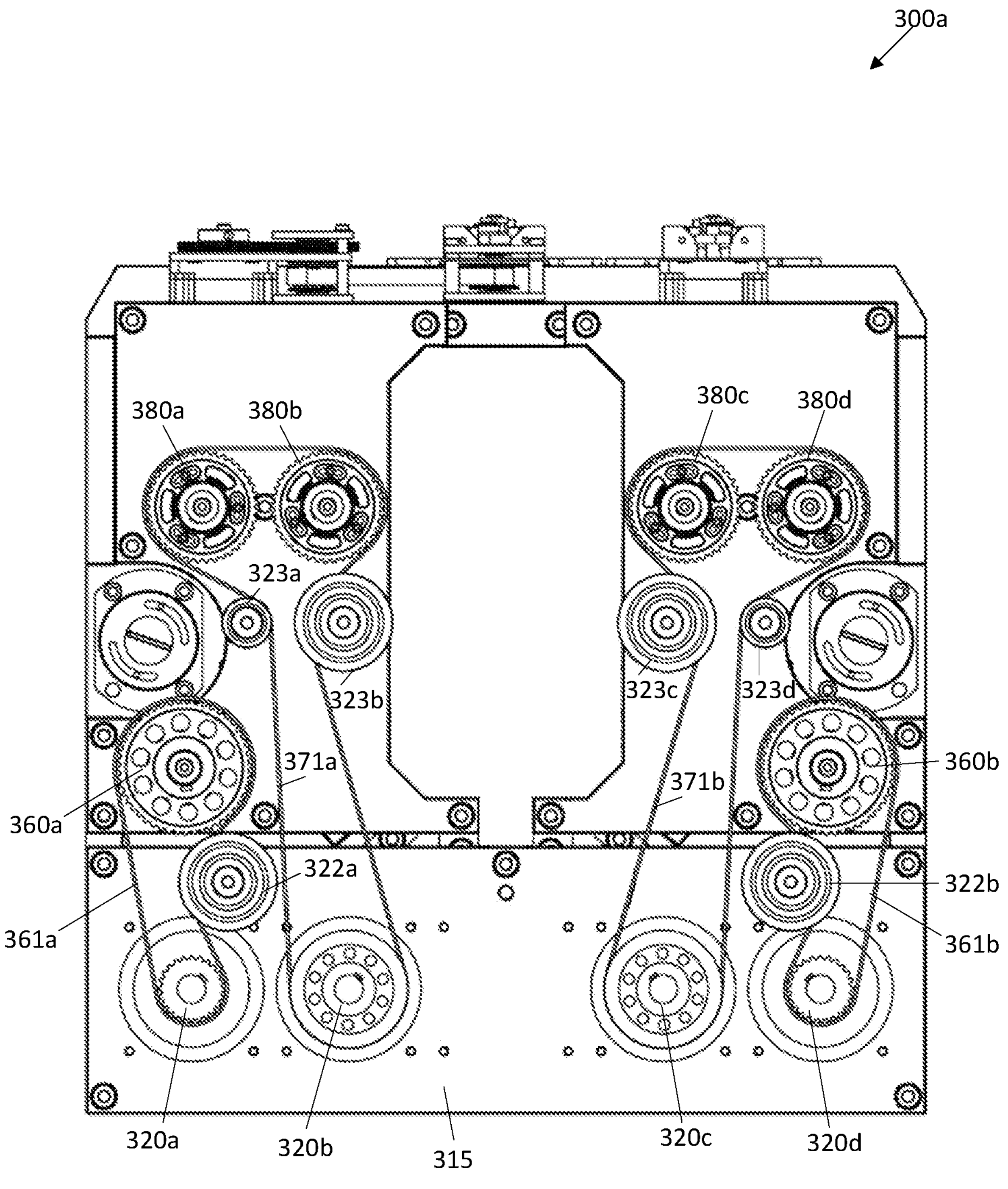
FIG. 13 is an end view of the transfer device of FIG. 9.

FIG. 13 illustrates an example implementation of the first end drive assembly 300*a*. As noted above, the end drive assemblies 300*a* and 300*b* are provided at the ends 101 and 102 of the transfer device 100. The end drive assemblies 300*a* and 300*b* are substantially mirror images of each other, and are preferably operated in concert with each other to control opposite ends of the transfer platform 250, the transfer belt 150, optional guard layer(s) 155*a* and 155*b*, etc. substantially simultaneously.

In the illustrated example, the end drive assembly 300*a*, first and second belt drive sprockets 320*a* and 320*d* are driven by motors 390*a* and 390*d*, respectively. The belt drive sprockets 320*a* and 320*d* are connected to transfer belt roller sprockets 360*a* and 360*b* by drive belts 361*a* and 361*b*, respectively. Rotation of the transfer belt roller sprockets 360*a* and 360*b* results in rotation of the transfer belt rollers 165*a* and 165*b*, respectively. In the illustrated example, tension idlers 322*a* and 322*b* are also provided to control the tension of drive belts 361*a* and 361*b*, respectively. It will be appreciated that the tension idlers 322*a* and 322*b* are optional.

Also shown are platform drive sprockets 320*b* and 320*c*, which are driven by motors 390*b* and 390*c*, respectively. The platform drive sprocket 320*b* is connected via a drive belt 371*a* to a first series of segment drive sprockets 380*a* and 380*b*. The platform drive sprocket 320*c* is connected via a drive belt 371*b* to a second series of segment drive sprockets 380*c* and 380*d*. Idlers 323*a* and 323*b* are provided in order to control tension on the drive belt 371*a*, and idlers 323*c* and 323*d* are provided in order to control tension on the drive belt 371*b*.

Figure 14:
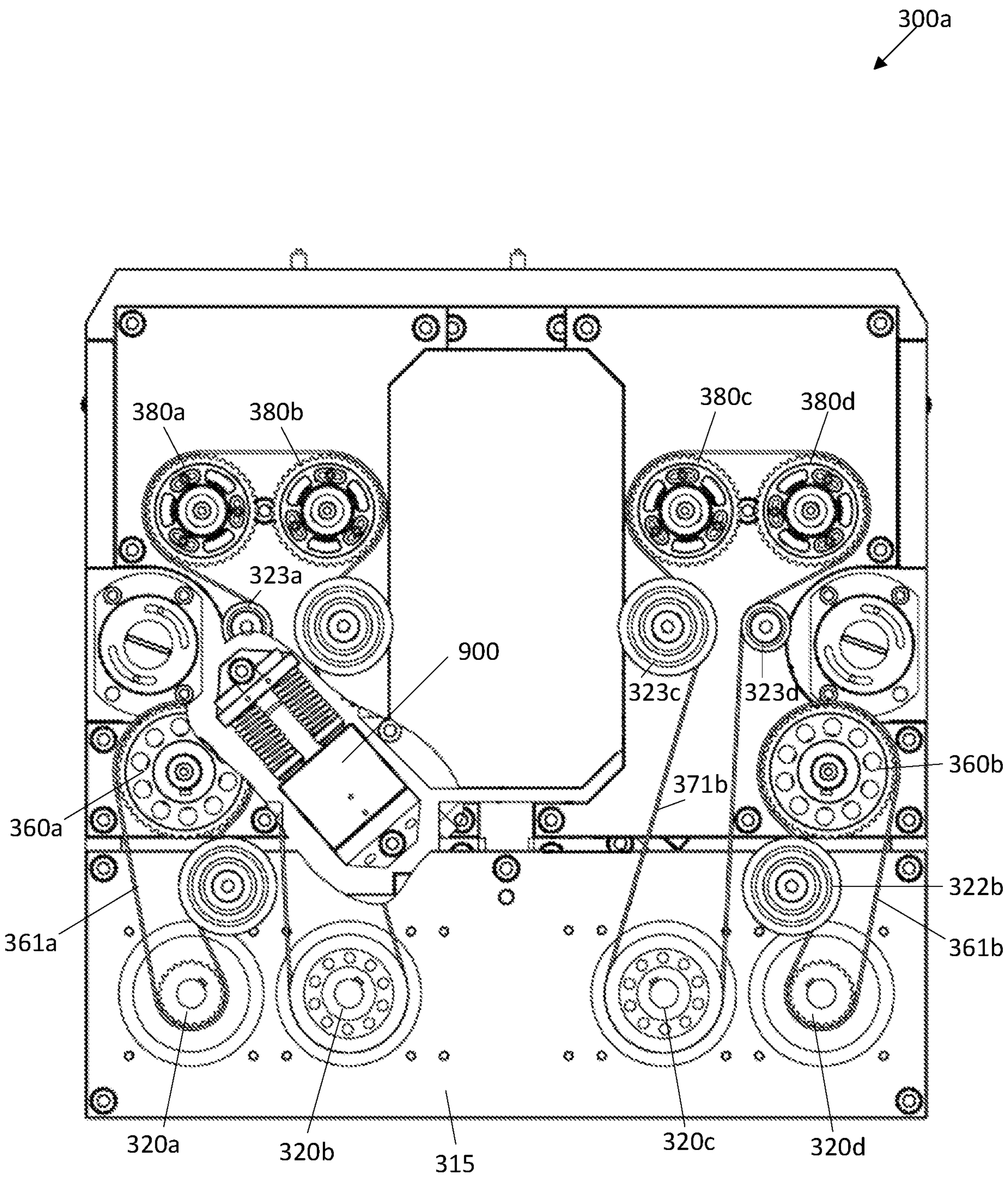
FIG. 14 is an end view of the transfer device of FIG. 9, with portions of support plates removed to show a belt tensioner assembly.
Figure 15B:
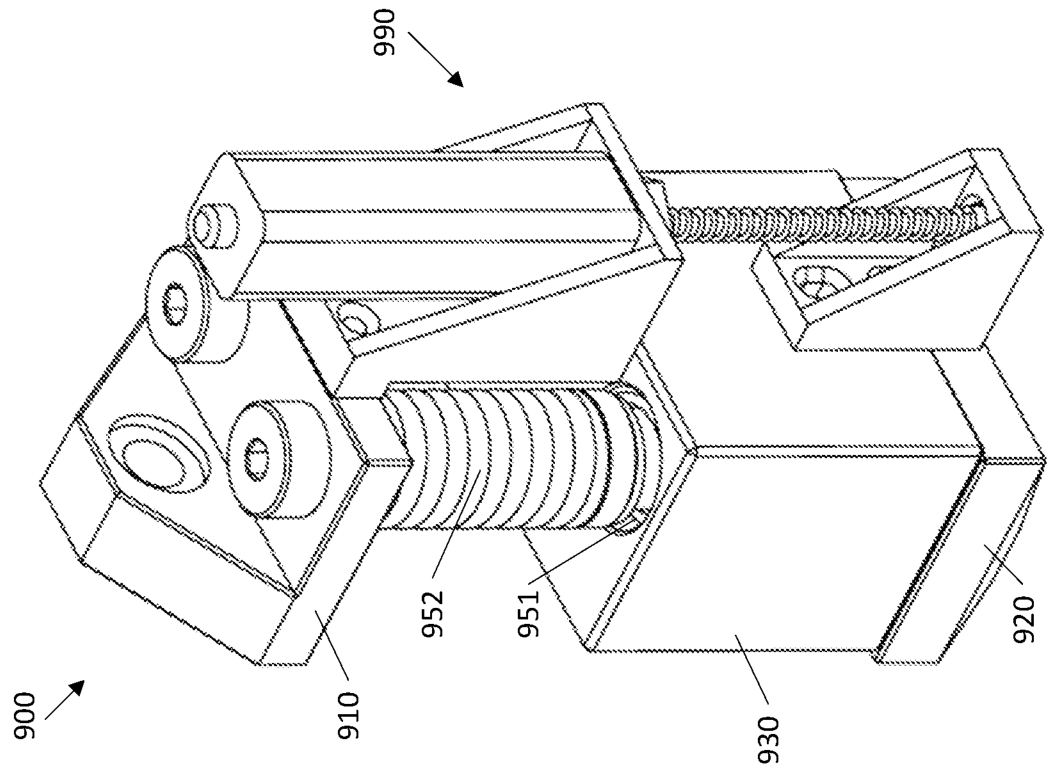
FIGS. 15A and 15B are perspective views of the belt tensioner assembly of FIG. 14.
Figure 15A:
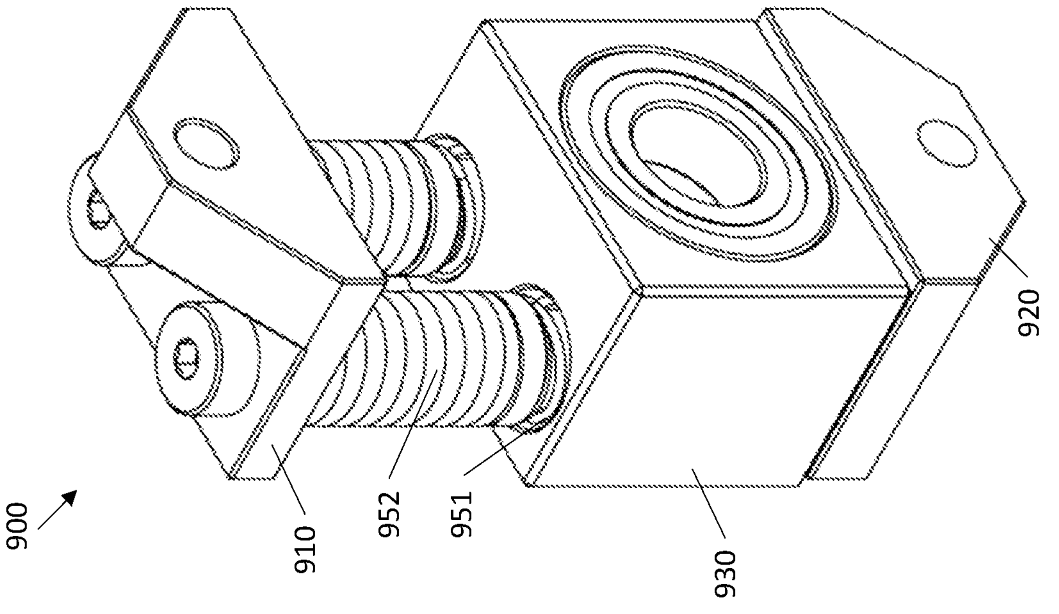

As illustrated in FIG. 14, a belt tensioner assembly 900 may be positioned between structural plates of an end drive assembly 300*a-b* (discussed further below). With reference to FIG. 15A, the belt tensioner assembly 900 includes a first frame member 910 secured in fixed relation to a second frame member 920 by shafts 940*a* and 940*b*. A movable frame member 930 can translate along shafts 940*a* and 940*b*. As illustrated in FIG. 15B, a linear displacement sensor 990 is attached to provide an output signal based on the relative position of the movable frame member 930.

Figure 16C:
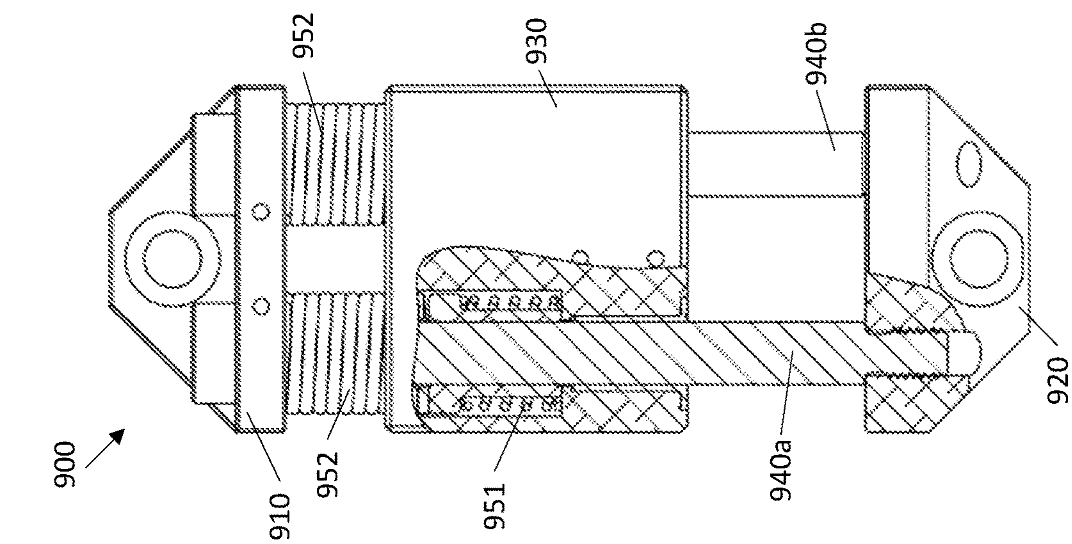
FIGS. 16A to 16C are partial section views of the belt tensioner assembly of FIG. 14.
Figure 16B:
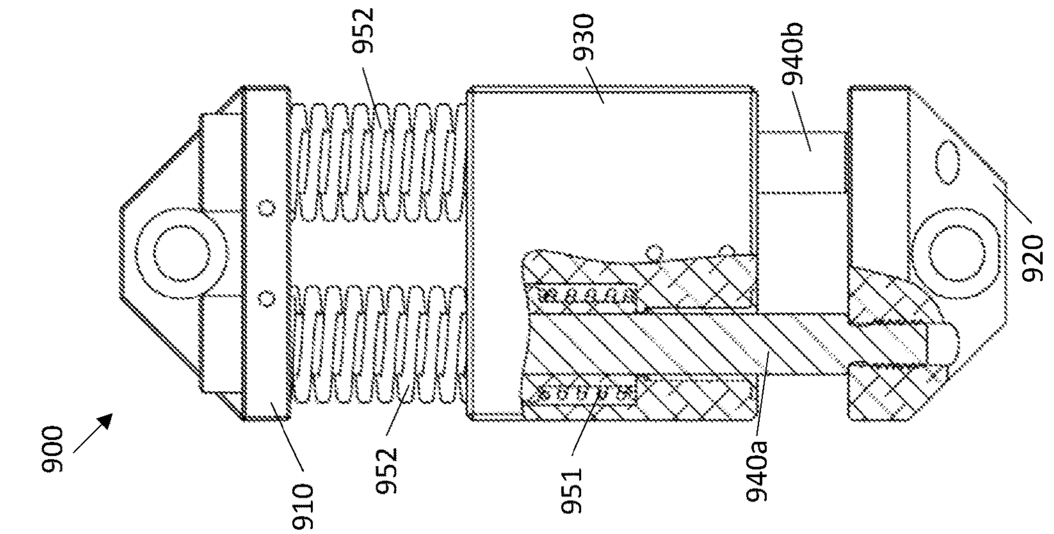
Figure 16A:
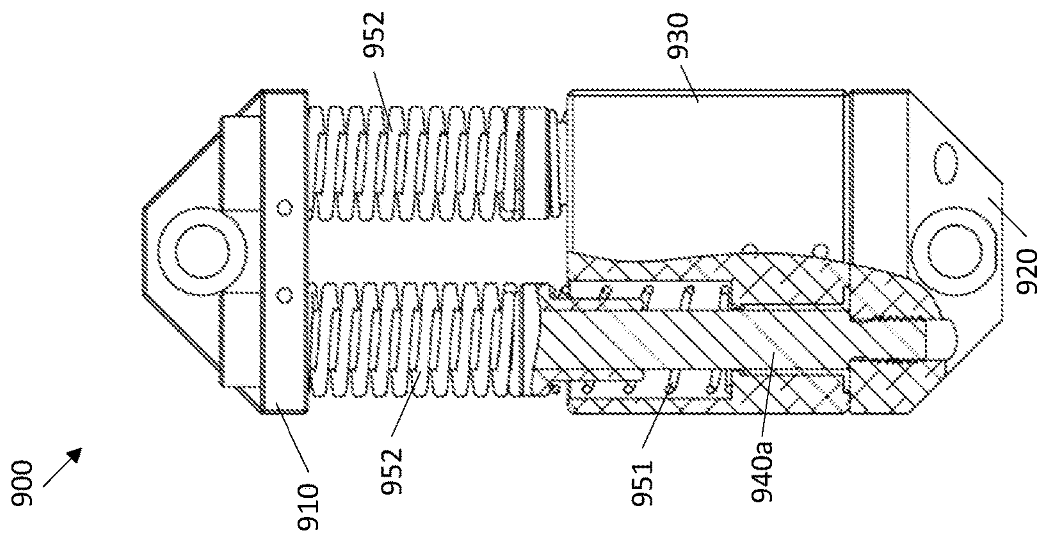

Turning to FIGS. 16A to 16C, in the illustrated example, the movable frame member 930 is biased towards second frame member 920. In the illustrated example, this bias is applied by first springs 951 and second springs 952 arranged in series, where the first and second springs have different stiffnesses or spring rates. As a result, during a first travel range of the movable frame member 930 (e.g. between the positions shown in FIGS. 16A and 16B), only springs with a lower relative spring rate (e.g. spring 951 in this example) will be deformed, while during a second travel range of the movable frame member 930 (e.g. between the positions shown in FIGS. 16B and 16C), both springs will be deformed, including springs with a higher relative spring rate (e.g. spring 952 in this example).

An advantage of this design is that it may allow the linear displacement sensor 990 to provide a high resolution signal both at relatively low transfer belt tensions (e.g. when no objects are in contact with transfer belt 150 and/or transfer platform 250), and at relatively high transfer belt tensions (e.g. when a patient is being transferred on the transfer platform 250).

In the illustrated example, each tensioner 165*a* and 165*b* is passively sprung. Alternatively, each tensioner 165*a* and 165*b* may be actively actuated, e.g. by providing a linear actuator instead of, or in addition to, one or more passive springs. Additionally, or alternatively, each tensioner 165*a* and 165*b* may be actively dampened, e.g. using ferro-dampening fluids or the like. In some implementations, the relative position of each tensioner 165*a* and 165*b* may be determined by a positioning sensor (not shown) such as a Time of Flight (TOF) or linear potentiometer, for example. This determined tensioner position may be used e.g. by the transfer device controller to measure and/or infer tension within the transfer belt 150.

In some implementations, each driven roller 160*a* and 160*b* is driven using a corresponding motor. It will be appreciated that any suitable motor type (e.g. stepper motors, DC or AC motors, brushless DC (BLDC) motors, pneumatic rotary motors, direct electrical motors, and the like) may be used in one or more variant implementations. Additionally, or alternatively, other gearing (e.g. two or more stages, planetary gearing) may be used. During operation, it will be appreciated that corresponding motors or actuators may be driven independently or synchronously to suit the required function(s).

As discussed above, the transfer belt 150 passes around the first transverse edge 213 of the platform plate 210 and around the second transverse edge 224 of platform plate 210. Optionally, some or all of the first and second transverse edges 213 and 224 may be provided with one or more friction-reducing features. With reference to FIG. 9, in the illustrated example, a number of rollers 255 are positioned along the second transverse edge 224 of the platform plate 210. Alternatively, or additionally, some or all surfaces proximate the first and second transverse edges 213 and 224 may be made from a low-friction material (e.g. Polytetrafluoroethylene (PTFE), Polyam ides, Graphite, Acetol, Ultra High Molecular Weight Polyethylene (UHMW PE), and/or have a low-friction coating applied thereto. Alternatively, or additionally, friction may be reduced via a controlled application of compressed air, one or more lubricants, captive ball bearings, or other suitable systems.

In some implementations, with reference back to FIG. 12A, flexible guard layers 155*a* and 155*b* are provided below the transfer belt 150 to inhibit or prevent direct contact between the transfer belt 150 and the surface on which the object being transferred to or from using the transfer platform 250. For example, as illustrated in FIG. 12A, a first guard layer 155*a* may be formed from a textile and/or flexible material with a first end 156*a* secured to the platform plate 210, and a second end 157*a* secured to a take-up roller 158*a*, which may be spring-biased and/or actively driven to take up the first guard layer 155*a* as the transfer platform 250*b* moves towards a retracted position. In the illustrated example, the first guard layer 155*a* passes over guide member 159*a*, which is secured to the end drive assembly 300*a*, such that guard layer 155*a* remains proximate the underside of the transfer platform 250*a* when the transfer platform 250*a* is in an extended position. A second guard layer 155*b* has a first end 156*b* secured to the platform plate 210, and a second end 157*b* secured to a take-up roller 158*b*, which may be substantially similar to the take-up roller 158*a*. Optionally, the flexible guard layers 155*a* and 155*b* may be formed from a low-friction material, e.g. Polytetrafluoroethylene (PTFE), Polyam ides, Graphite, Acetol, Ultra High Molecular Weight Polyethylene (UHMW PE), and the like.

Figure 12B:
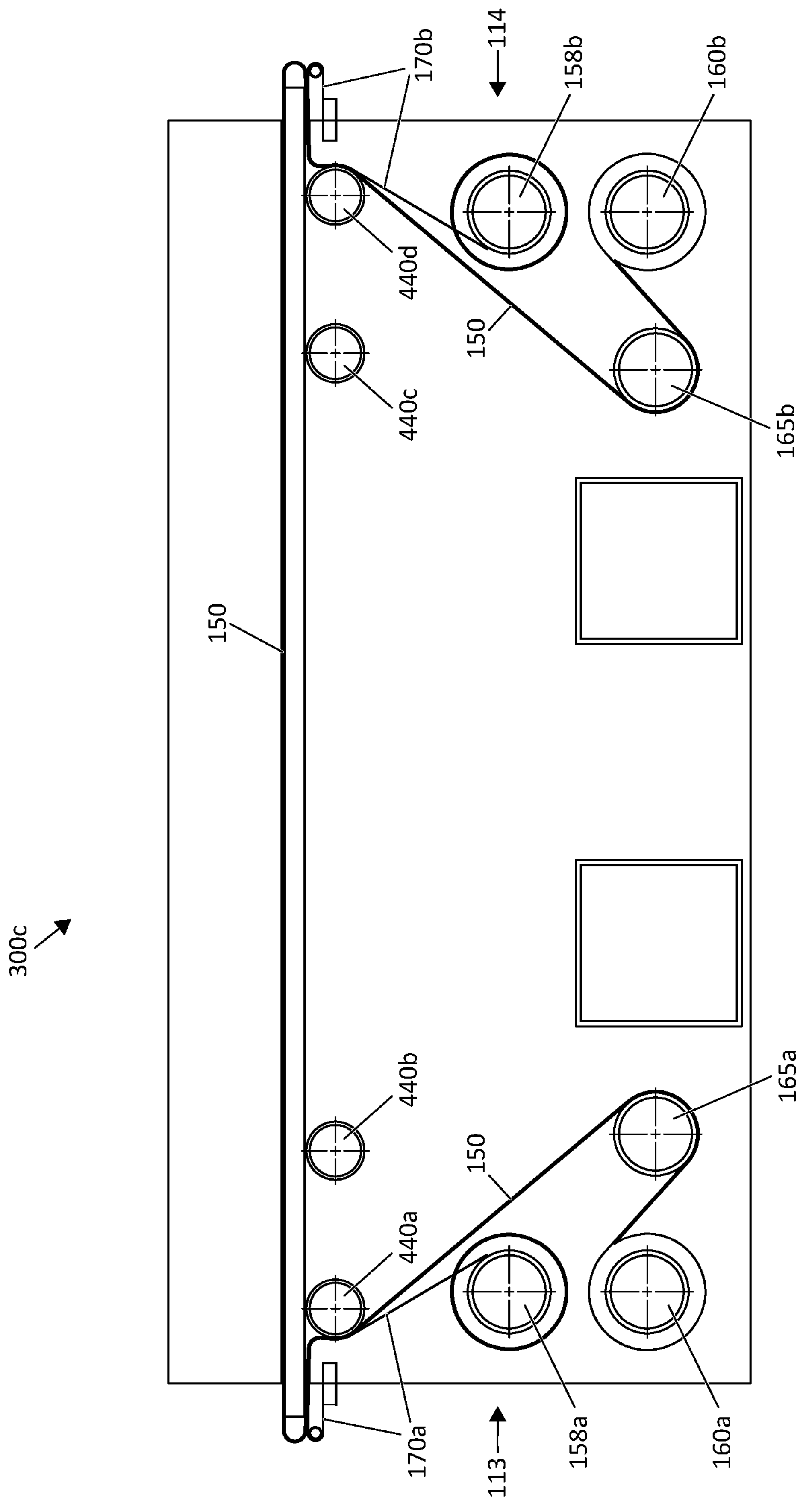
FIG. 12B is a schematic view of a transfer belt path of the transfer device of FIGS. 7A to 7E.

With reference to FIG. 12B, shown is a schematic view of a transfer belt path of the transfer device of FIGS. 7A to 7E. An end drive assembly 300*c* has a belt path for the first transfer belt 150 that is similar to what is shown in FIG. 12A. Much like in FIG. 12A, the transfer belt 150 extends from the first roller 160*a* around idler 165*a*, around a top surface of the transfer platform, around idler 165*b*, and onto a second roller 160*b*. However, note that the first transfer belt 150 is not routed between the shafts 440*a* and 440*b* and the shafts 440*c* and 440*d*. Also note that there is a second transfer belt 170*a* and a third transfer belt 170*b*. The second transfer belt 170*a* extends from roller 158*a*, and the third transfer belt 170*b* extends from roller 158*b*. In some implementations, the second transfer belt 170*a* and the third transfer belt 170*b* are both passive (e.g. spring loaded, using multi-rotation torsion springs) and are not connected to any actuator or device controller. In other implementations, the second transfer belt 170*a* and the third transfer belt 170*b* are coupled to actuators that are operably coupled to the transfer device controller.

Figure 17:
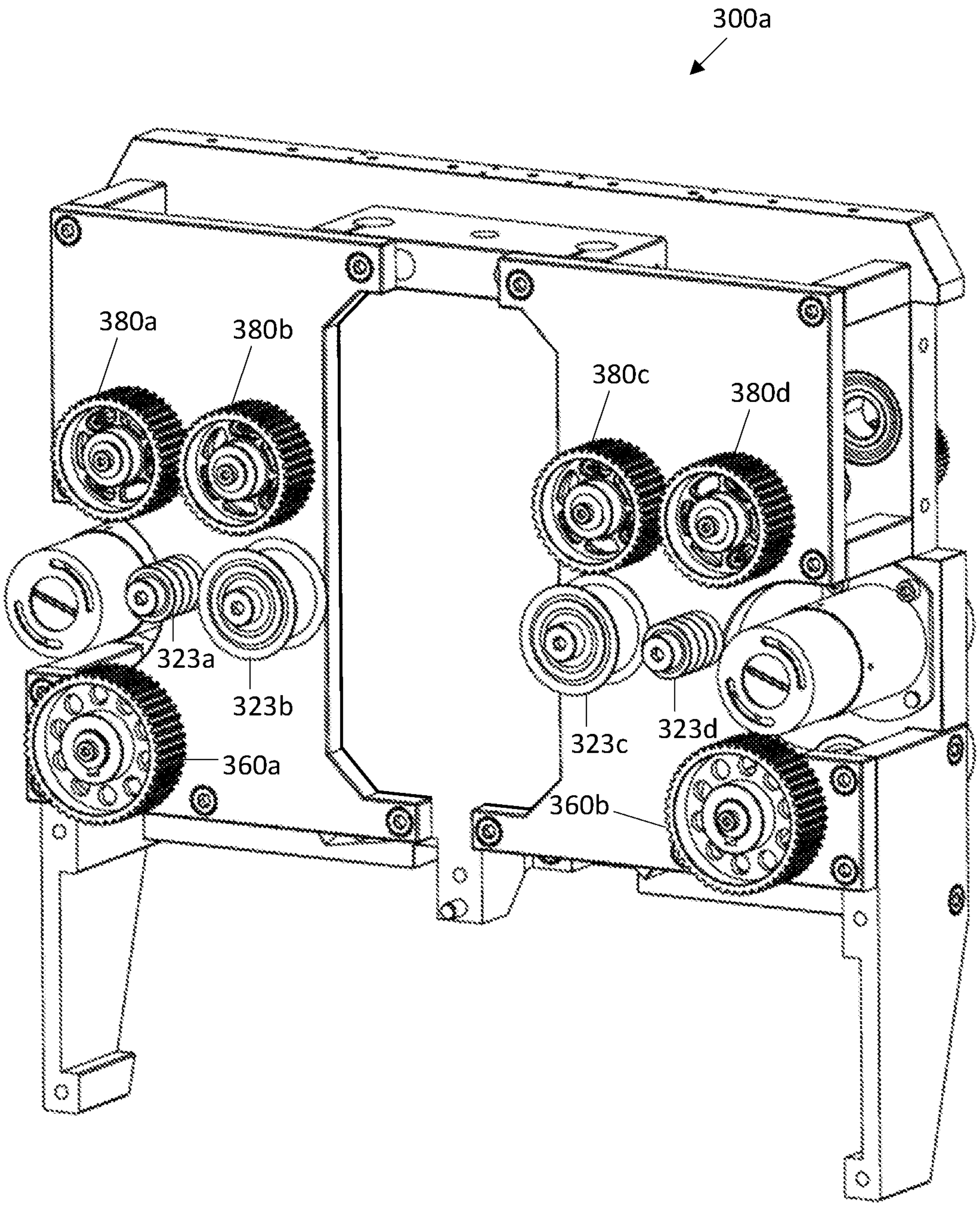
FIG. 17 is a perspective view of an outer side of an end drive assembly of the transfer device of FIG. 9 with a motor assembly and drive belts omitted for clarity.
Figure 18:
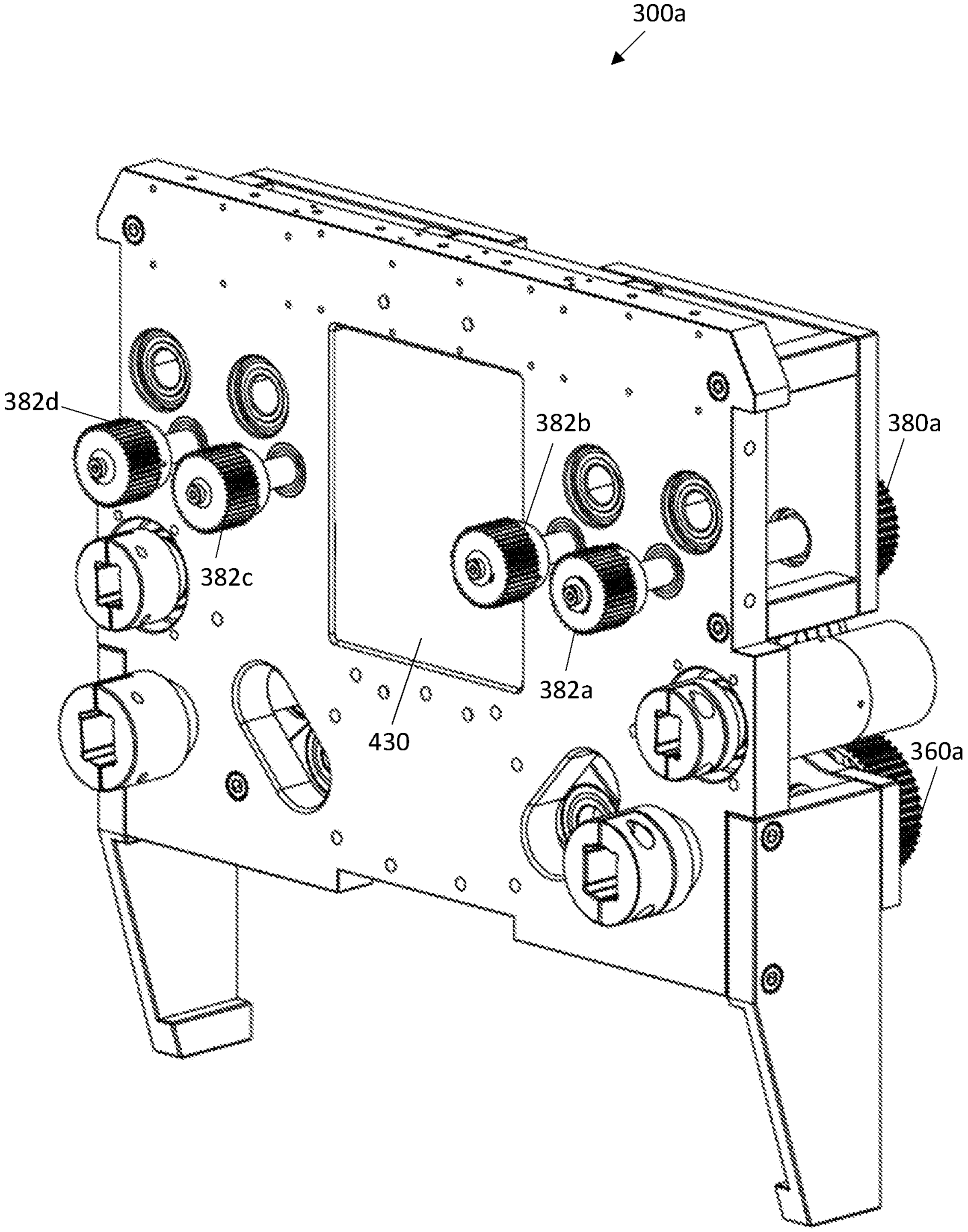
FIG. 18 is a perspective view of an inner side of the end drive assembly of FIG. 17.

FIG. 17 is a perspective view of an outer side of an end drive assembly 300*a* of the transfer device 100 of FIG. 9 with a motor assembly and drive belts omitted for clarity. FIG. 18 illustrates an inner side of the end drive assembly 300*a*. In the illustrated example, platform drive pinions 382*a-d* are provided at an upper end of the platform. These drive pinions 382*a-d* are connected to segment drive sprockets 380*a-d*, respectively (see e.g. FIG. 13).

In the illustrated example, teeth of platform drive pinions 382*a-d* engage platform rack segments (not shown) provided on the underside of the ends of the platform plate 210. It will be appreciated that in one or more alternative implementations, the engagement between the end drive assembly 300*a* and the platform plate 210 may not include a rack and pinion arrangement. For example, platform drive rollers may have a compressible elastomer configured to provide a sufficiently high frictional coefficient between themselves and the undersides of the ends of the platform plate 210.

Figure 19:
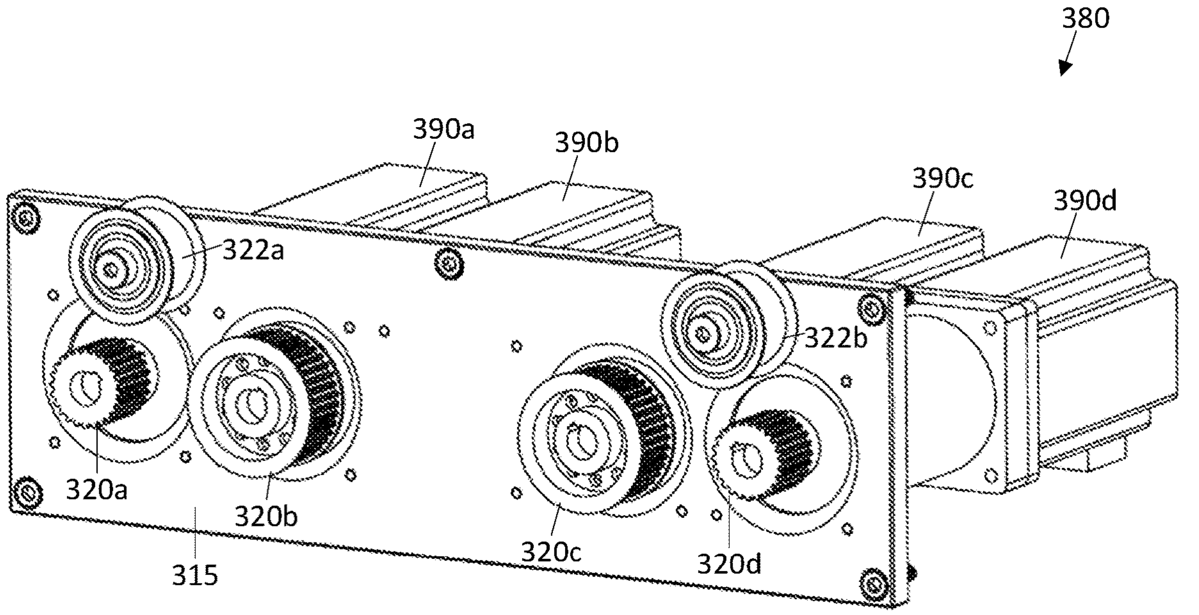
FIGS. 19 and 20 are perspective views of a motor assembly for the end drive assembly of FIGS. 17 and 18.
Figure 20:
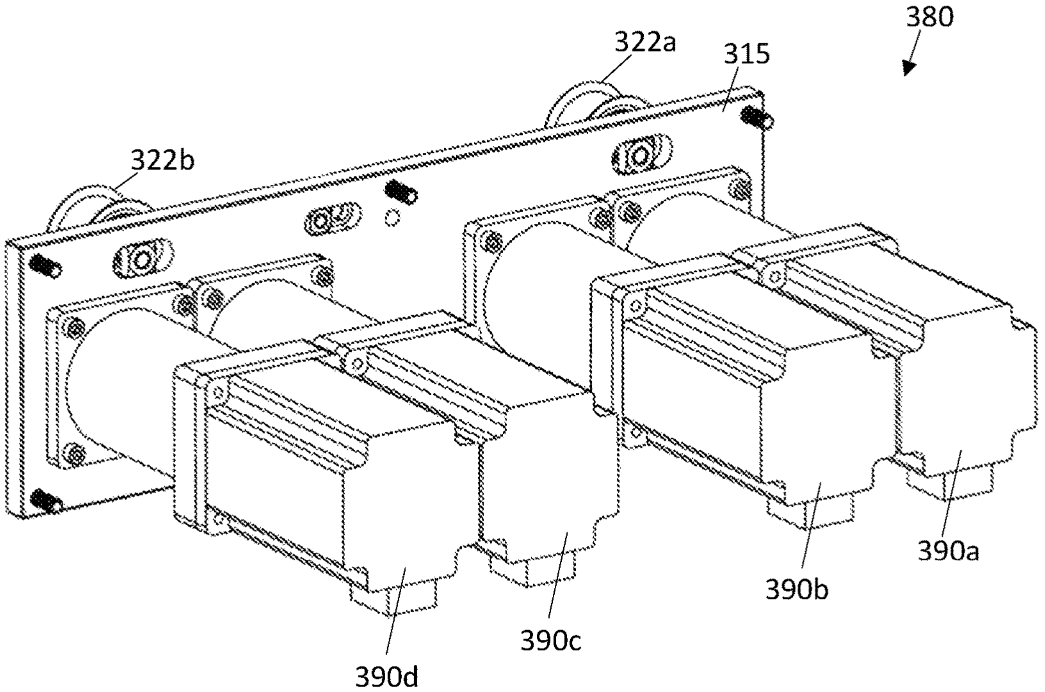

FIGS. 19 and 20 illustrate an example of a motor hub assembly 380. In the illustrated example, a motor baseplate 315 supports motors 390*a-d*. Two of the motors 390*a* and 390*d* are connected to the belt drive sprockets 320*a* and 320*d* and via one or more linear driveshafts, and two of the motors 390*b* and 390*c* are connected to the platform drive sprockets 320*b* and 320*c* in a similar manner. Also, the tension idlers 322*a* and 322*b* are illustrated as being mounted on the motor base plate 315.

Enabling the motor hub assembly 380 to be modular may have one or more advantages. For example, allowing an entire set of motors and drive wheels to be 'swapped out' may facilitate easier maintenance and/or service of the transfer device 100, which may lead to reduced downtime of the transfer device 100.

In the examples illustrated in FIGS. 1 to 20, the transfer platform 250 is supported by the device body 110 when in a retracted position, and are cantilevered from the device body 110 when extended (partially or fully). For example, with reference to FIG. 12A, the platform plate 210 is supported by the rollers 440*a-d* when in a retracted position.

FIGS. 21A to 21D illustrate an example embodiment of the transfer device 100 that includes platform extension supports 570*a-b* that can be used to increase the width of the supported (i.e. non-cantilevered) surface. Such a design may have one or more advantages. For example, it may provide increased patient comfort and or safety when using the transfer device 100 to move a patient resting on the platform from one room to another.

Figure 21A:
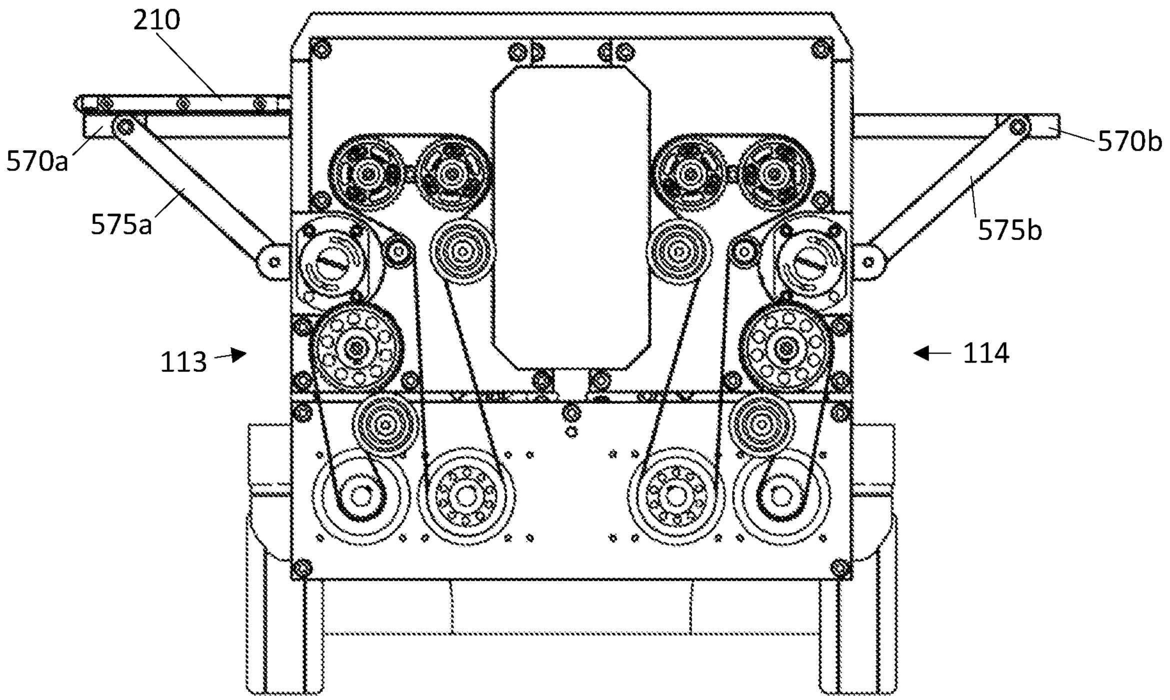
FIGS. 21A to 21D are schematics showing platform extension supports of a transfer device in accordance with another embodiment.
Figure 21B:
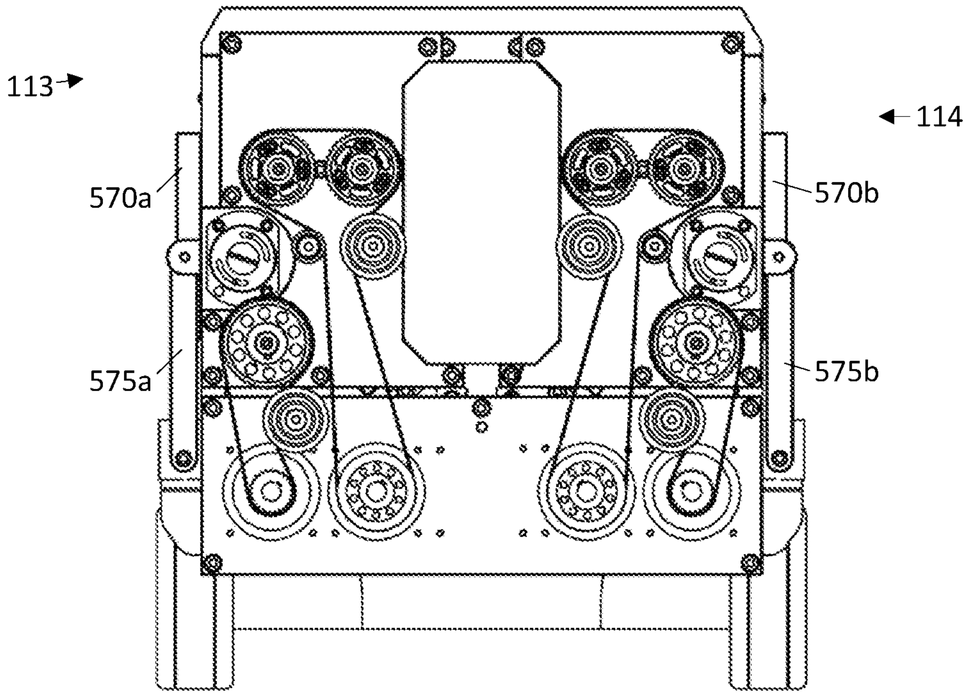
Figure 21C:
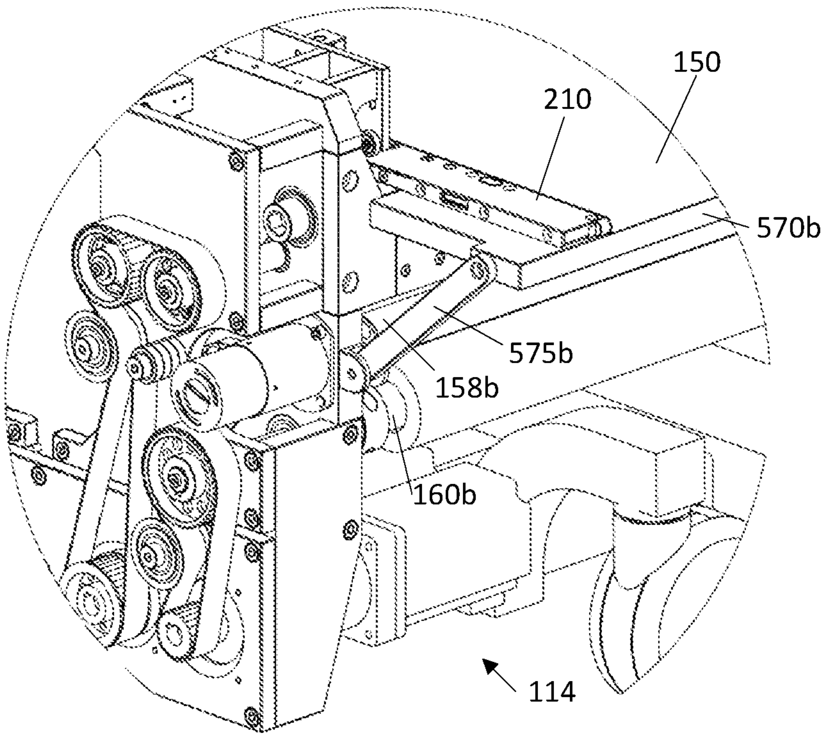

With reference to FIGS. 21A and 21C, a first platform extension support 570*a* extends outwardly from the first side 113 of the device body 110, and a second platform extension support 570*b* extends outwardly from the second side 114 of the device body 110. In the illustrated example, each platform extension support 570*a-b* is supported by one or more support arms 575. The support arms 575 are connected to the device body 110 below their respective platform extension supports 570, and provide vertical support for the platform extension supports 570 and the transfer platforms 250 resting thereon.

Figure 21D:
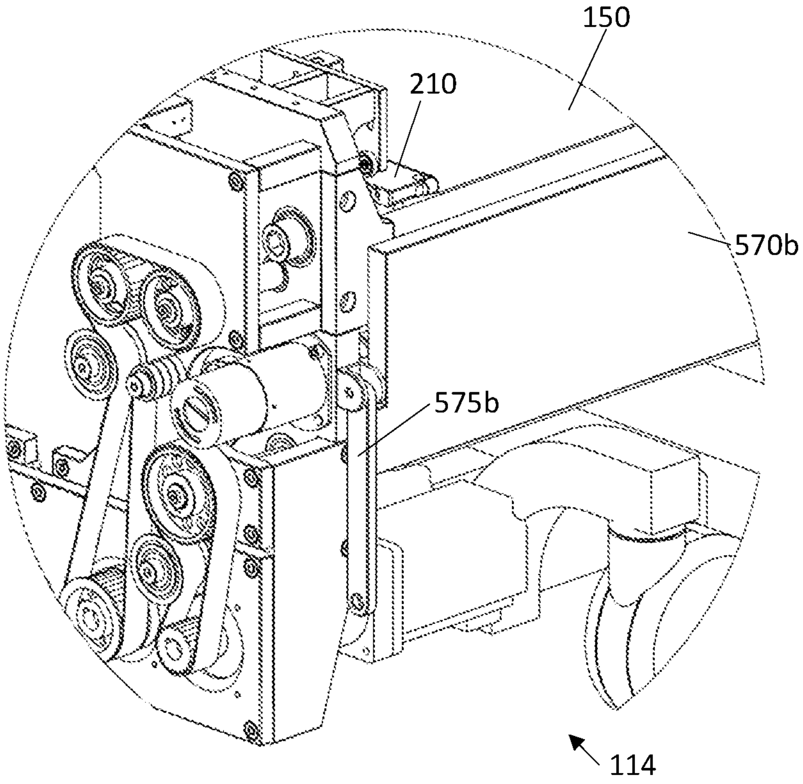

With reference to FIGS. 21B and 21D, in the illustrated example each platform extension support 570*a-b* is pivotally connected to the device body 110 (e.g. using a hinge or other suitable connection) and each support arm 575 is pivotally connected to the device body 110 and releasably securable to the platform extension support 570*a-b*. An advantage of this design is that the platforms extension supports 570*a-b* can be folded inwardly when not needed, for example as shown in FIGS. 21B and 21D, to provide a smaller storage footprint for the transfer device 100.

In the illustrated example, the platform extension supports 570*a-b* are generally rectangular planar support surfaces. It will be appreciated that in one or more alternative implementations, platform extension supports may be of different shapes and/or may have different surface features. For example, one or more rollers may be provided on an upper surface of a platform extension support.

Also, in the illustrated example, the platform extension supports 570*a-b* may be manually moved between the positions shown in FIGS. 21A and 21C, and the positions shown in FIGS. 21B and 21D. In one or more alternative implementations, one or more platform extension support actuators (either ‘passive’ actuators, such as gas springs, hydraulic drag cylinders, and the like, or ‘active’ actuators, such as linear, pneumatic, or hydraulic actuators) may be provided to extend and/or retract platform extension supports automatically, e.g. via a control system of the transfer device 100.

Referring now to FIGS. 22A to 22F, shown are schematics of a locking mechanism to selectively detach the second and third transfer belts. A main purpose for selectively detaching the second and third transfer belts is to enable the platform plate 210 and first transfer belt 150 to dynamically cross-over-center from the first side 113 of the device body 110 to the second side 114 of the device body 110, and vice-versa, even while there is a patient or object on top of the platform plate 210. Although FIGS. 22A to 22F focus on a locking mechanism on the second side 114 of the device body 110 for the third transfer belt 170*b*, it is noted that there would be a corresponding locking mechanism on the first side 113 of the device body 110 for the second transfer belt 170*a*.

Figure 22A:
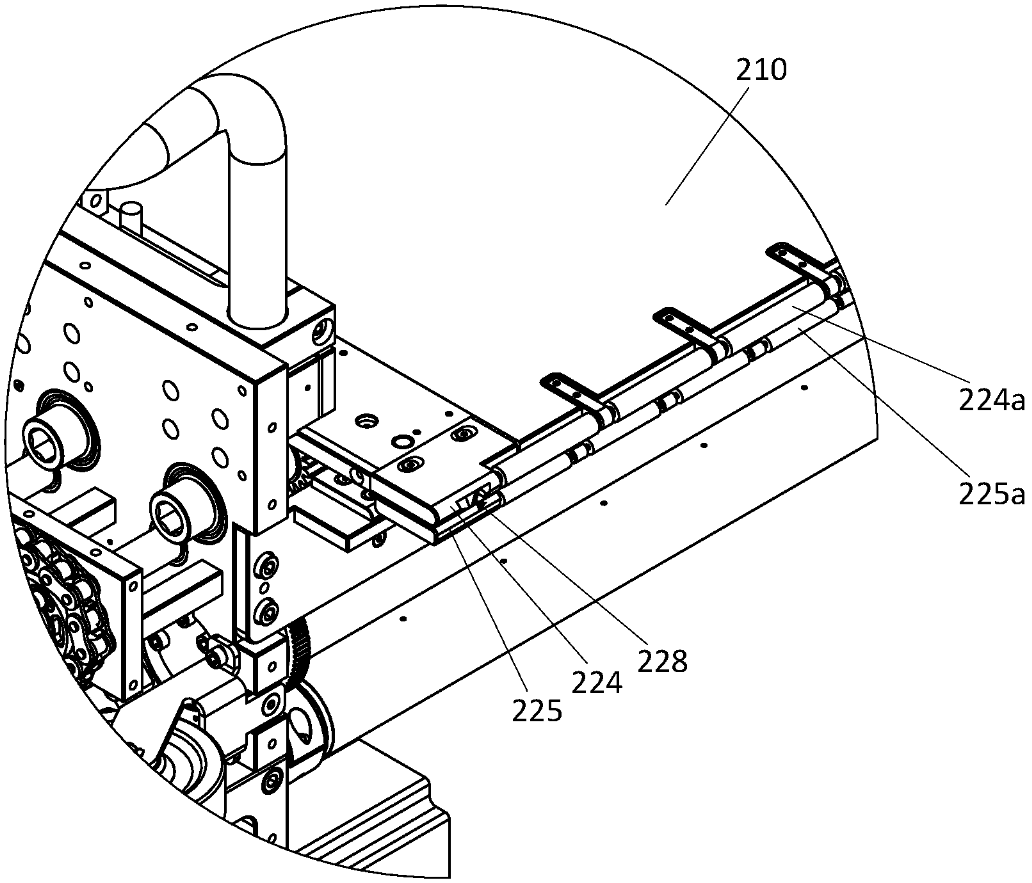
FIGS. 22A to 22F are schematics of a locking mechanism to selectively detach and attach second and third transfer belts.

With reference to FIG. 22A, the second transverse edge 224 of the platform plate 210 includes a detachable member 225 for the third transfer belt 170*b*. In some implementations, the second transverse edge 224 has rollers 224*a* over which the first transfer belt 150 can move whilst mitigating friction, and the detachable member 225 likewise has rollers 225*a* over which the third transfer belt 170*b* can move whilst mitigating friction. In some implementations, each end of the detachable member 225 selectively attaches to the second transverse edge 224 of the platform plate 210 using a dovetail joint 228. With reference to FIG. 22E, the dovetail joint 228 can be tapered such that the detachable member 225 can slide off in only one direction which occurs when the platform plate 210 crosses over from being centered in the device body 110 (see FIG. 22C) to the first side 113 of the device body 110 (see FIG. 22E). Other attachment means are possible.

Figure 22B:
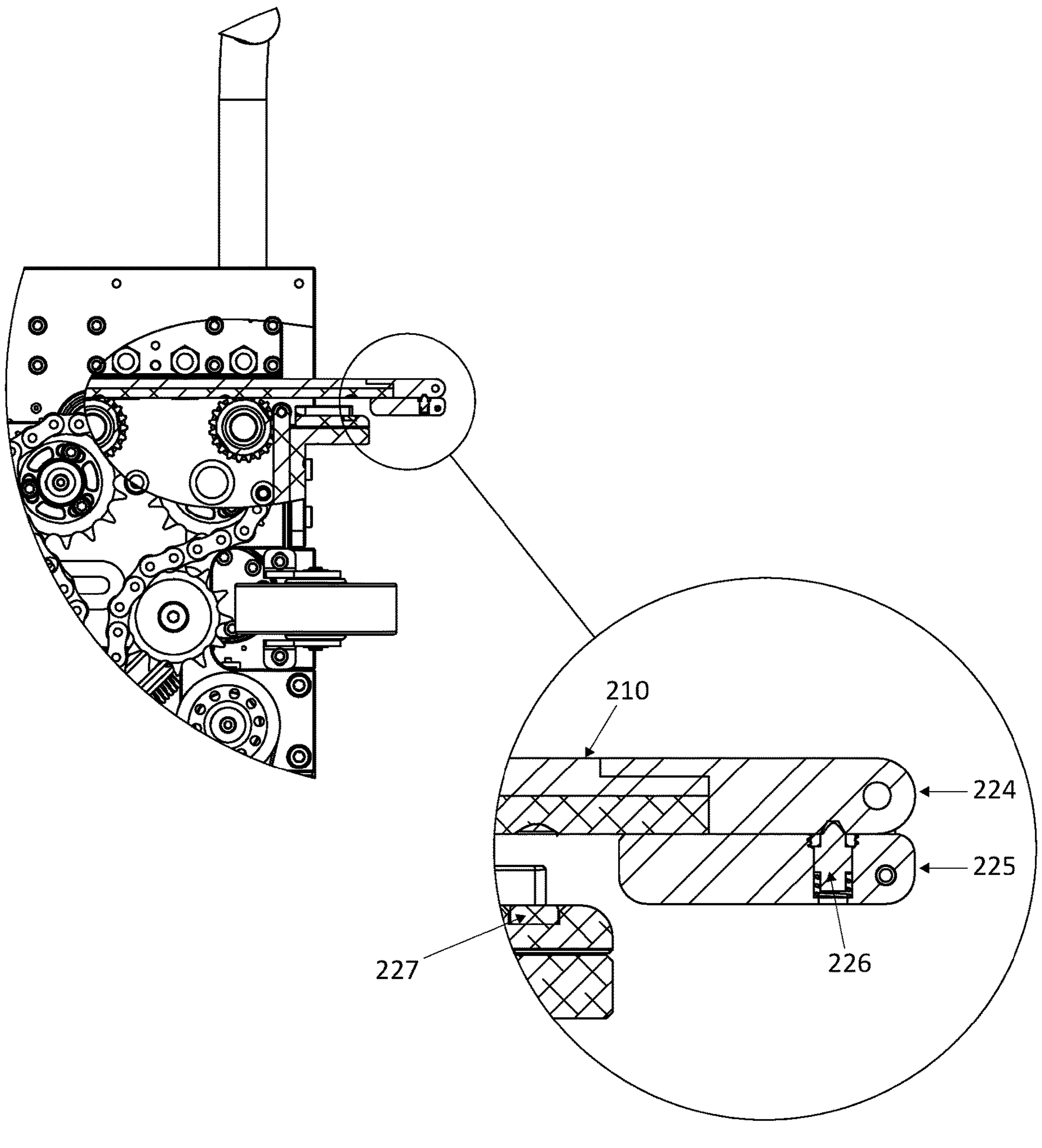
Figure 22C:
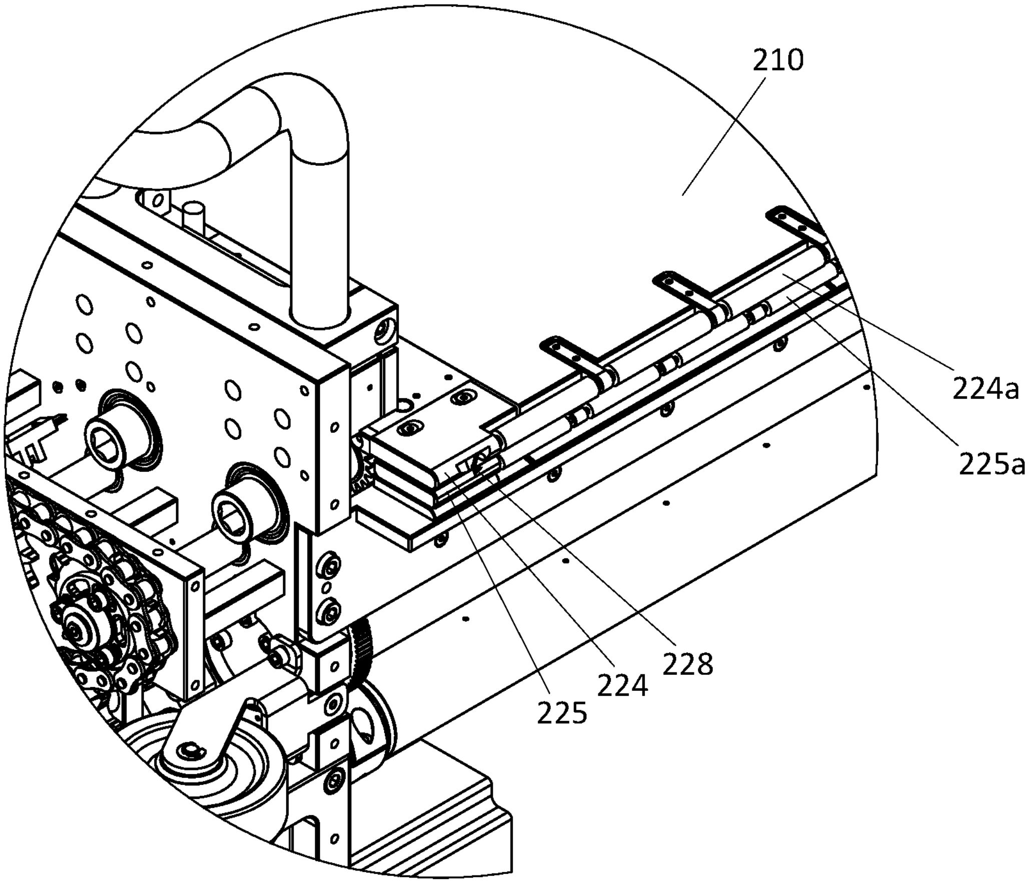
Figure 22D:
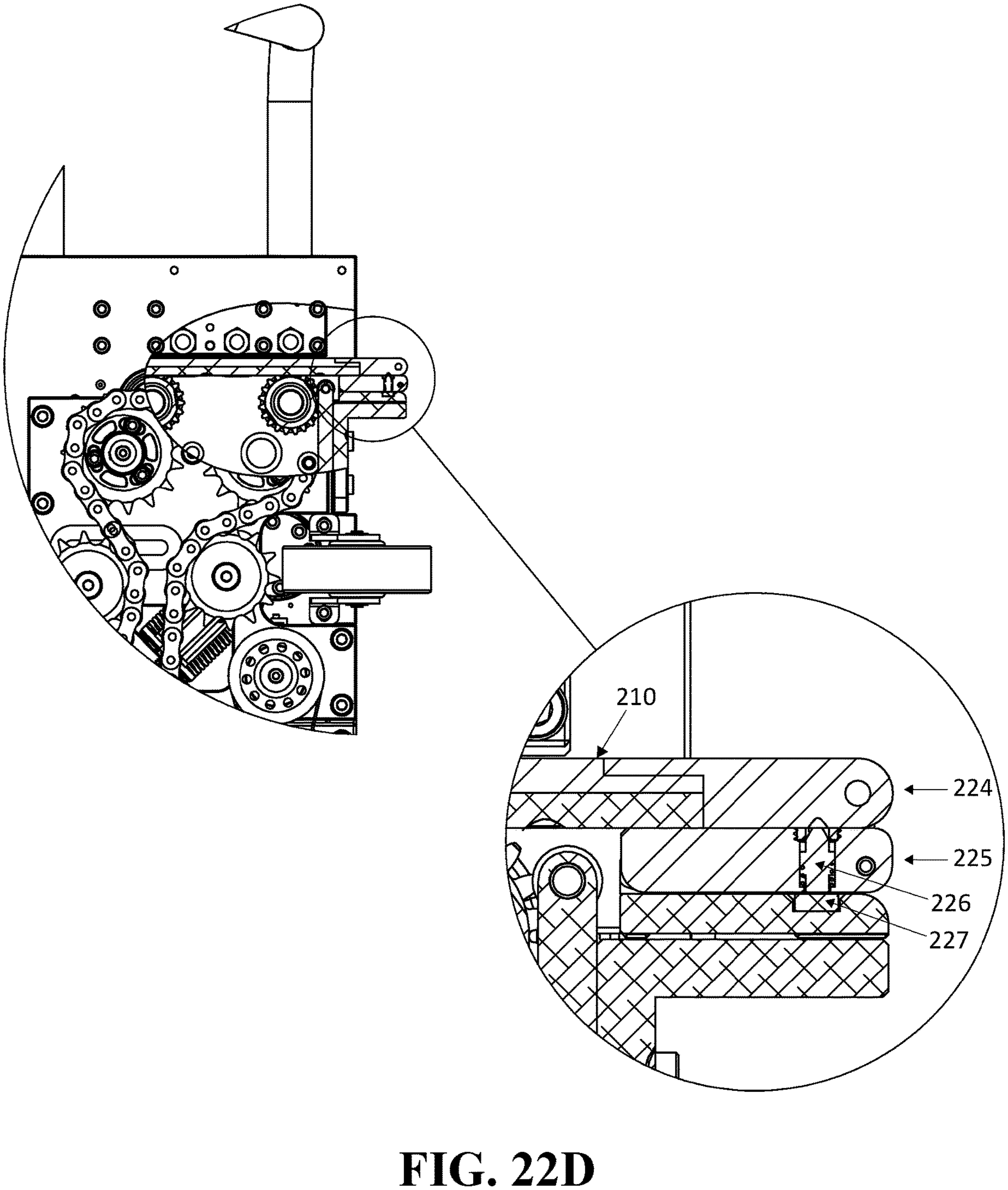
Figure 22E:
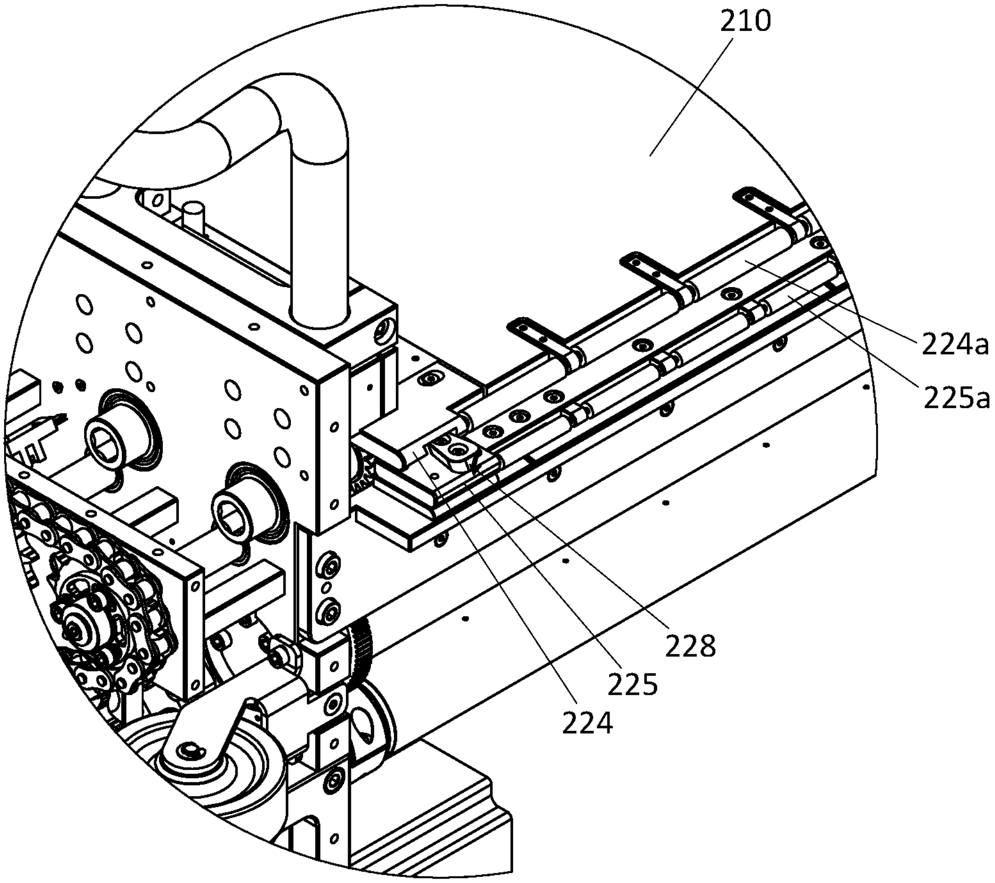
Figure 22F:
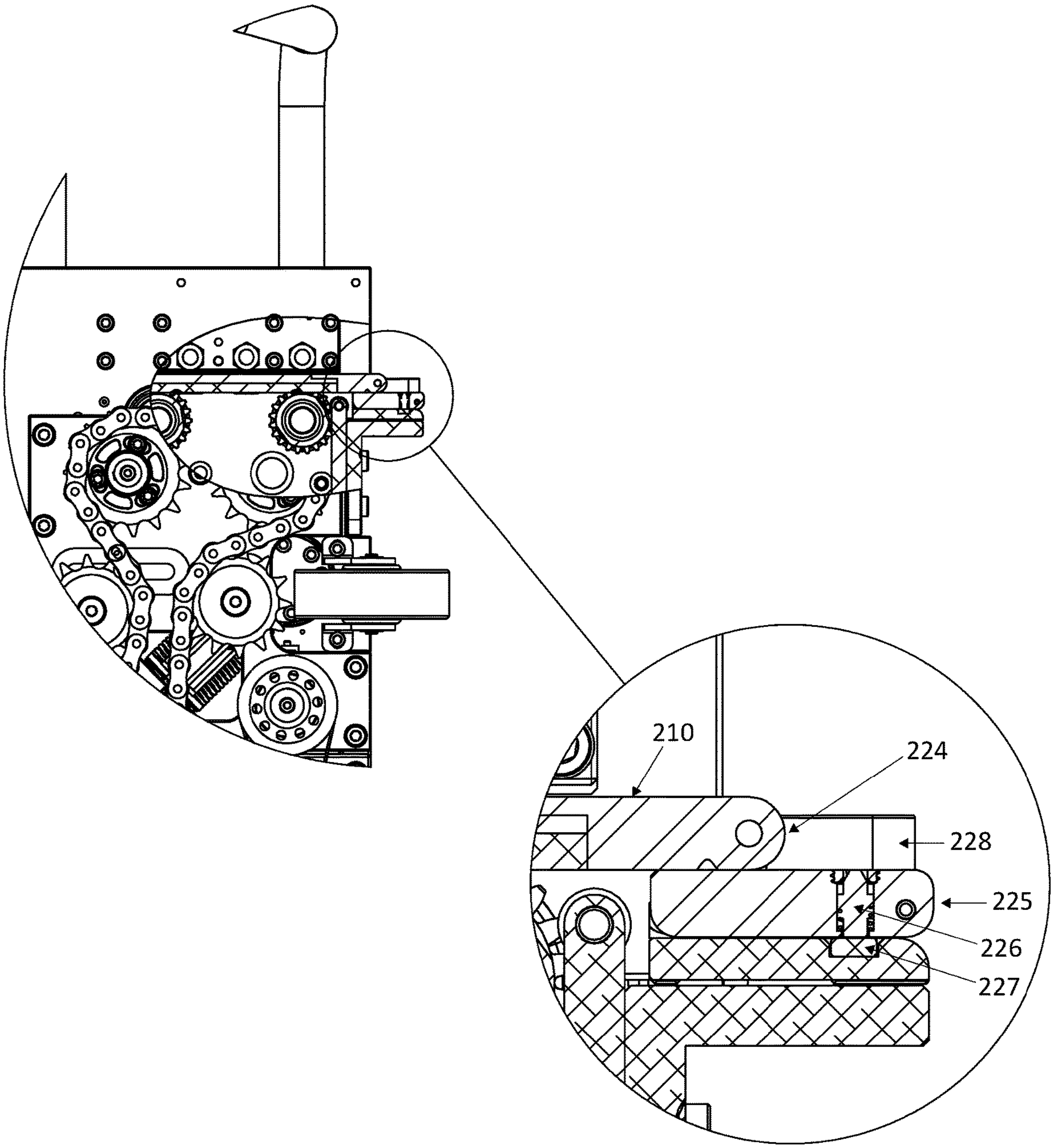

In some implementations, each end of the detachable member 225 has a spring-loaded magnet 226 that generally has two states: a first state shown in FIG. 22B in which the spring-loaded magnet 226 is pushed by a spring into a corresponding hole in the platform plate 210 while the detachable member 225 is fixed to the second transverse edge 224, and a second state shown in FIGS. 22D and 22F in which the spring-loaded magnet 226 is pulled down by magnetic force into a recess 227 while the platform plate 210 is either centered in the device body 110 (see FIG. 22D) or has crossed over to the first side 113 of the device body 110 (see FIG. 22F). The spring-loaded magnet 226 can help to ensure that the detachable member 225 remains fixed to the device body 110 when the detachable member 225 becomes detached from the platform plate 210.

It is noted that the spring-loaded magnet 226 is one of many possibilities for selectively securing the detachable member 225 to the device body 110. Referring now to FIGS. 23A to 23G, shown are schematics of another locking mechanism to selectively detach second and third transfer belts. FIGS. 23A to 23G illustrate an implementation which is entirely mechanical without any magnets. Although FIGS. 23A to 23G focus on a locking mechanism on the first side 113 of the device body 110 for the second transfer belt 170*a*, it is noted that there would be a corresponding locking mechanism on the second side 114 of the device body 110 for the third transfer belt 170*b*.

Figure 23A:
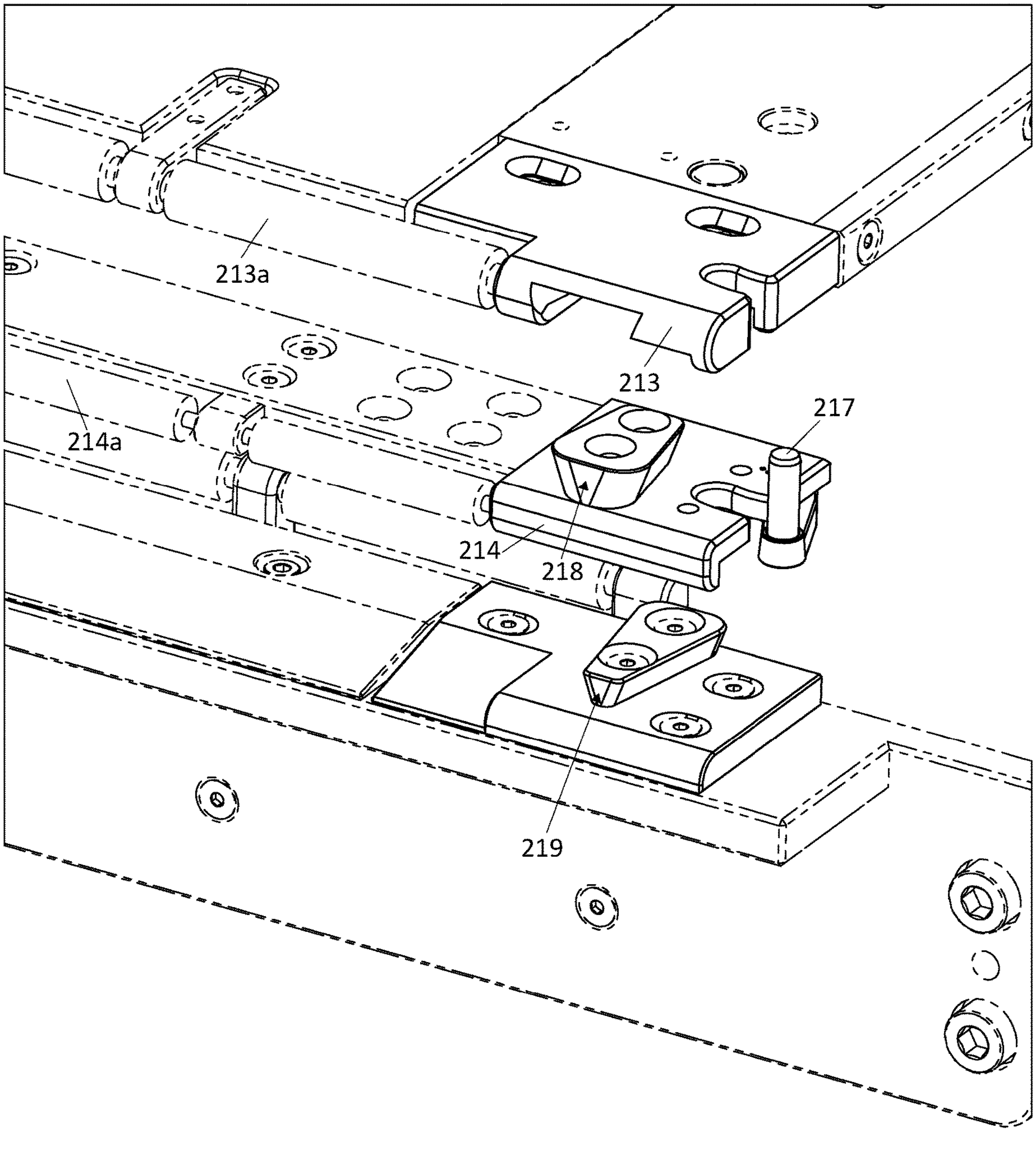
FIGS. 23A to 23G are schematics of another locking mechanism to selectively detach and attach second and third transfer belts.
Figure 23B:
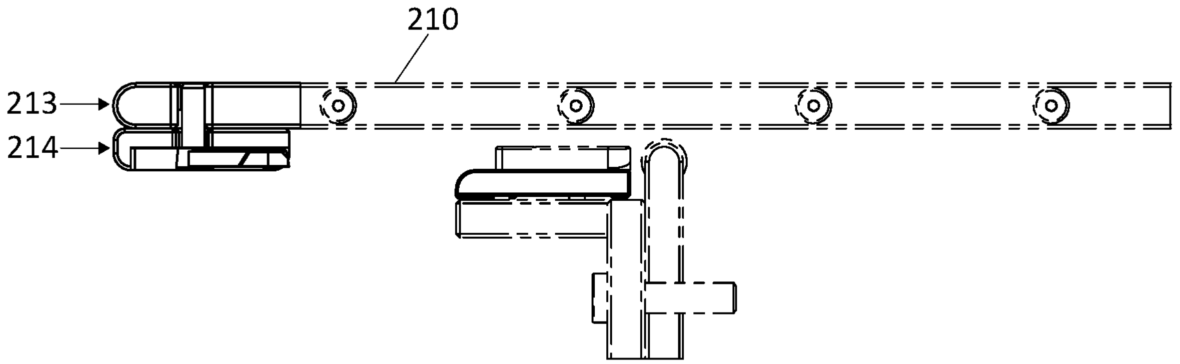
Figure 23C:
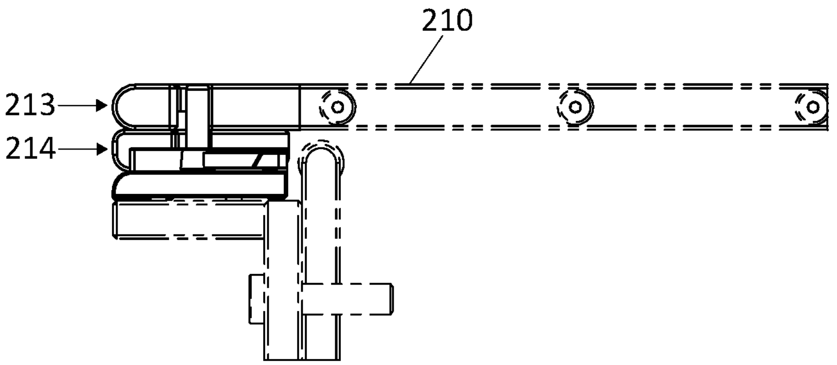
Figure 23D:
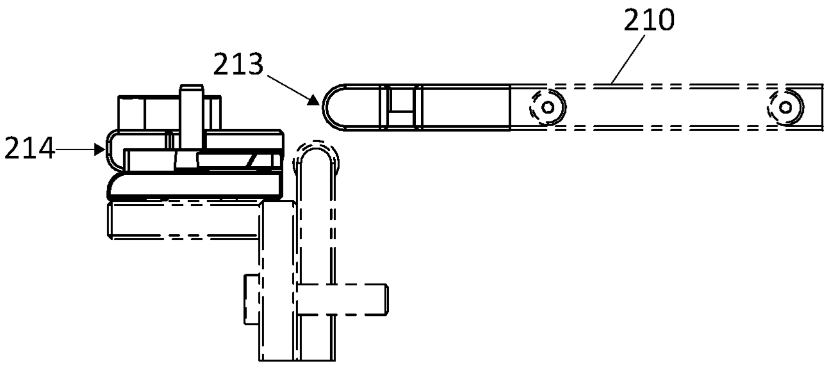

With reference to FIG. 23A, the first transverse edge 213 of the platform plate 210 includes a detachable member 214 for the second transfer belt 170*a*. In some implementations, the first transverse edge 213 has rollers 213*a* over which the first transfer belt 150 can move whilst mitigating friction, and the detachable member 214 likewise has rollers 214*a* over which the second transfer belt 170*a* can move whilst mitigating friction. In some implementations, each end of the detachable member 214 selectively attaches to the first transverse edge 213 of the platform plate 210 using a dovetail joint 218. The dovetail joint 218 can be tapered such that the detachable member 214 can slide off in only one direction which occurs when the platform plate 210 crosses over from being centered in the device body 110 (see FIG. 23C) to the second side 114 of the device body 110 (see FIG. 23D). Other attachment means are possible.

In some implementations, with reference back to FIG. 23A, each end of the detachable member 214 can be selectively attached to the device body 110 using another dovetail joint 219. The dovetail joint 219 can be tapered such that the detachable member 214 can slide off in only one direction which occurs when the platform plate 210 crosses over from being centered in the device body 110 (see FIG. 23C) to the first side 113 of the device body 110 (see FIG. 23B). The dovetail joint 219 can help to ensure that the detachable member 214 remains fixed to the device body 110 when the detachable member 214 becomes detached from the platform plate 210.

Figure 23E:
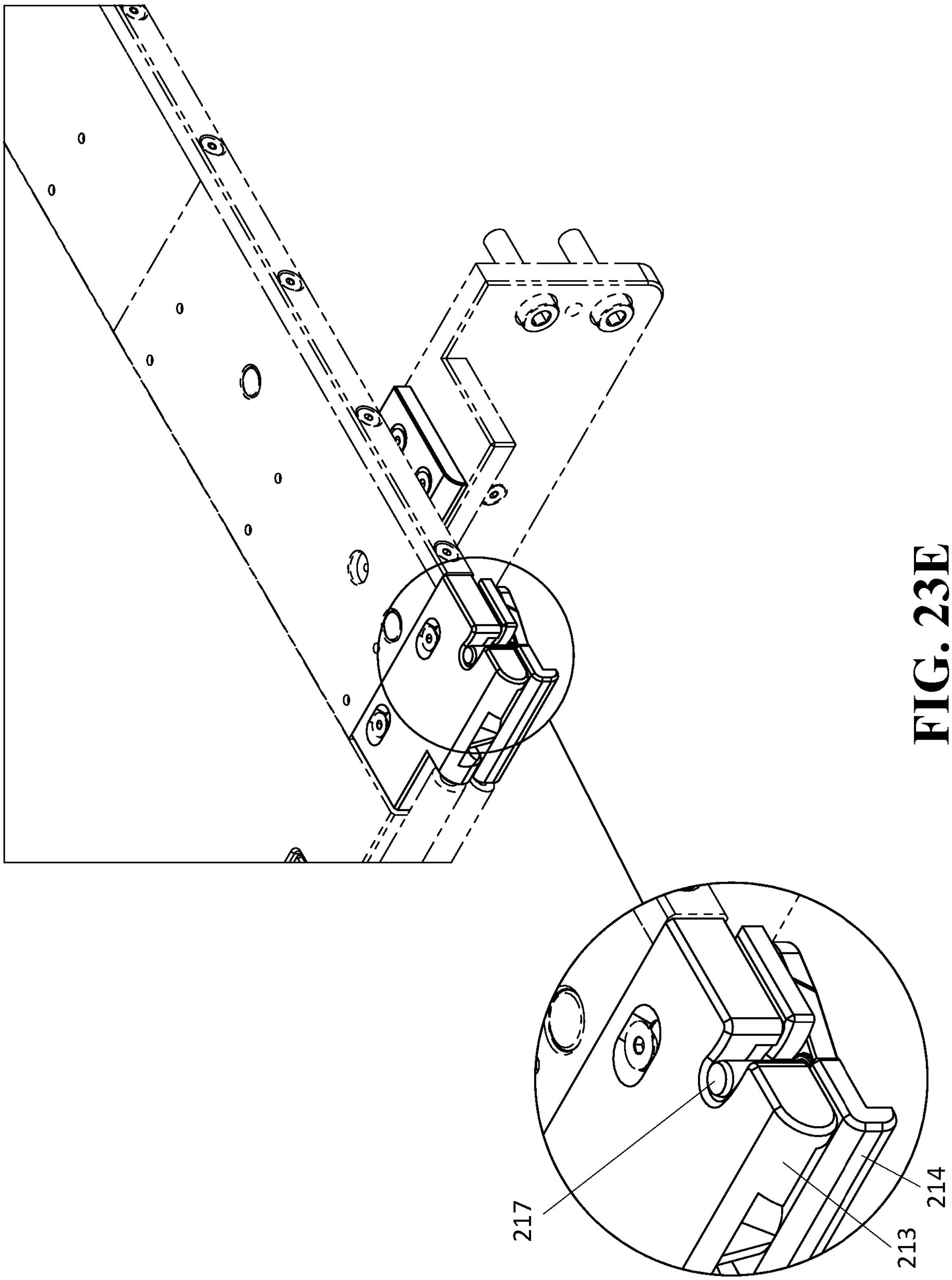
Figure 23F:
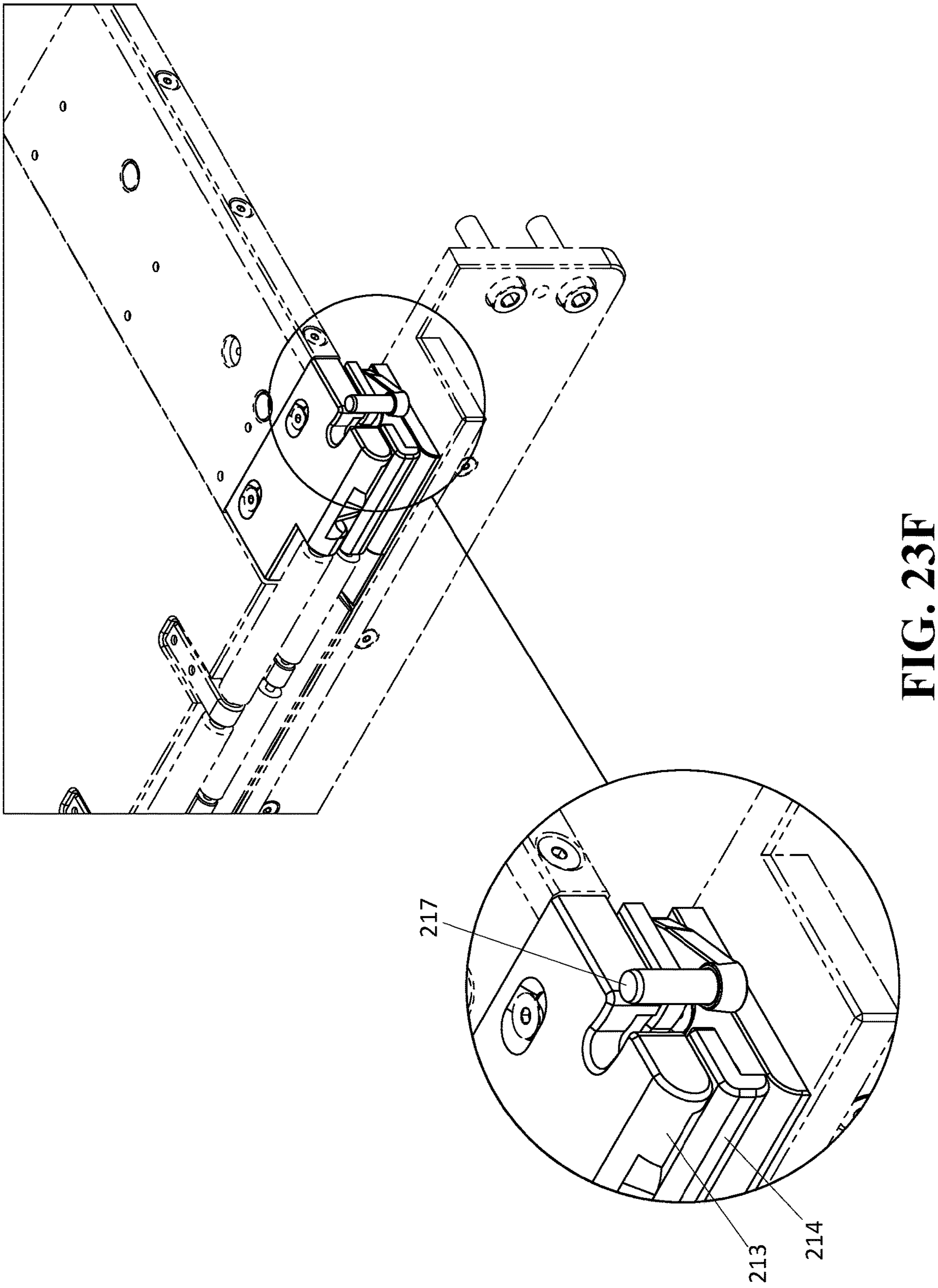
Figure 23G:
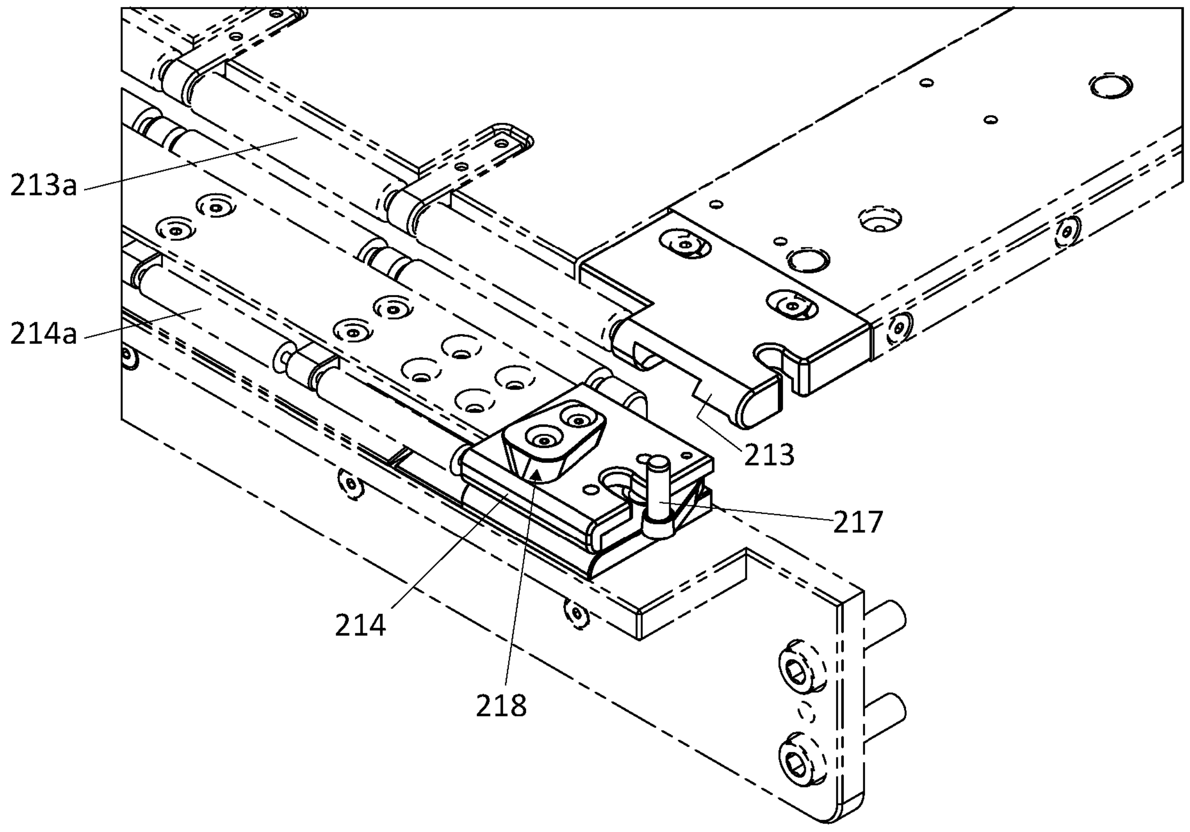

In some implementations, with reference to FIGS. 23E to 23G, each end of the detachable member 214 has a pin 217 that can mechanically pivot into and out of a corresponding slot of the first transverse edge 213. This can help to secure the detachable member 214 to the first transverse edge 213.

Note that the locking mechanisms depicted and described with reference to FIGS. 22A to 22F and FIGS. 23A to 23G are very specific and are provided merely for exemplary purposes. Components such as dovetail joints, spring-laded magnets, and pins can be present in specific implementations. More generally, there can be provided a first locking mechanism configured to selectively attach the second transfer belt 170*a* to the first transverse edge 213 of the platform plate 210 for the first extended position and to selectively detach the second transfer belt 170*a* from the platform plate 210 for the second extended position, and a second locking mechanism configured to selectively attach the third transfer belt 170*b* to the second transverse edge 224 of the platform plate 210 for the second extended position and to selectively detach the third transfer belt 170*b* from the platform plate 210 for the first extended position.

In some implementations, the transfer device 100 includes one or more treatment systems (e.g. transfer belt treatment systems and/or platform plate treatment system) for applying a cleaning and/or disinfecting treatment to one or more of the transfer belts 150 and 170*a-b* and/or to the platform plate 210. There are many possibilities for the treatment systems. For example, as described in more detail below, the transfer device 100 can include one or more of ultraviolet (UV) treatment systems, fluid spray treatment systems, fluid bath treatment system, contact cleaning systems, or any combination thereof. Specific examples are described below with reference to FIGS. 24A-D, but it to be understood that the transfer device can be configured to include features of any or all of the example treatment systems shown in FIGS. 24A-D.

In some implementations, the transfer device 100 has at least one ultraviolet (UV) light emitter positioned within the device housing to continuously or selectively emit UV light towards an upper surface of the transfer belt 150, or both an upper surface and a lower surface of the first transfer belt 150, as it passes by the UV light emitter(s). Additionally, or alternatively, at least one UV light emitter is positioned within the transfer device 100 to continuously or selectively emit UV light towards the second and third transfer belts 170*a-b* as they pass by the UV light emitter(s). Additionally, or alternatively, at least one UV light emitter is positioned within the transfer device 100 to continuously or selectively emit UV light towards the platform plate 210 as the platform plate 210 pass by the UV light emitter(s). Such a configuration may be characterized as an ultraviolet germicidal irradiation system.

Figure 24A:
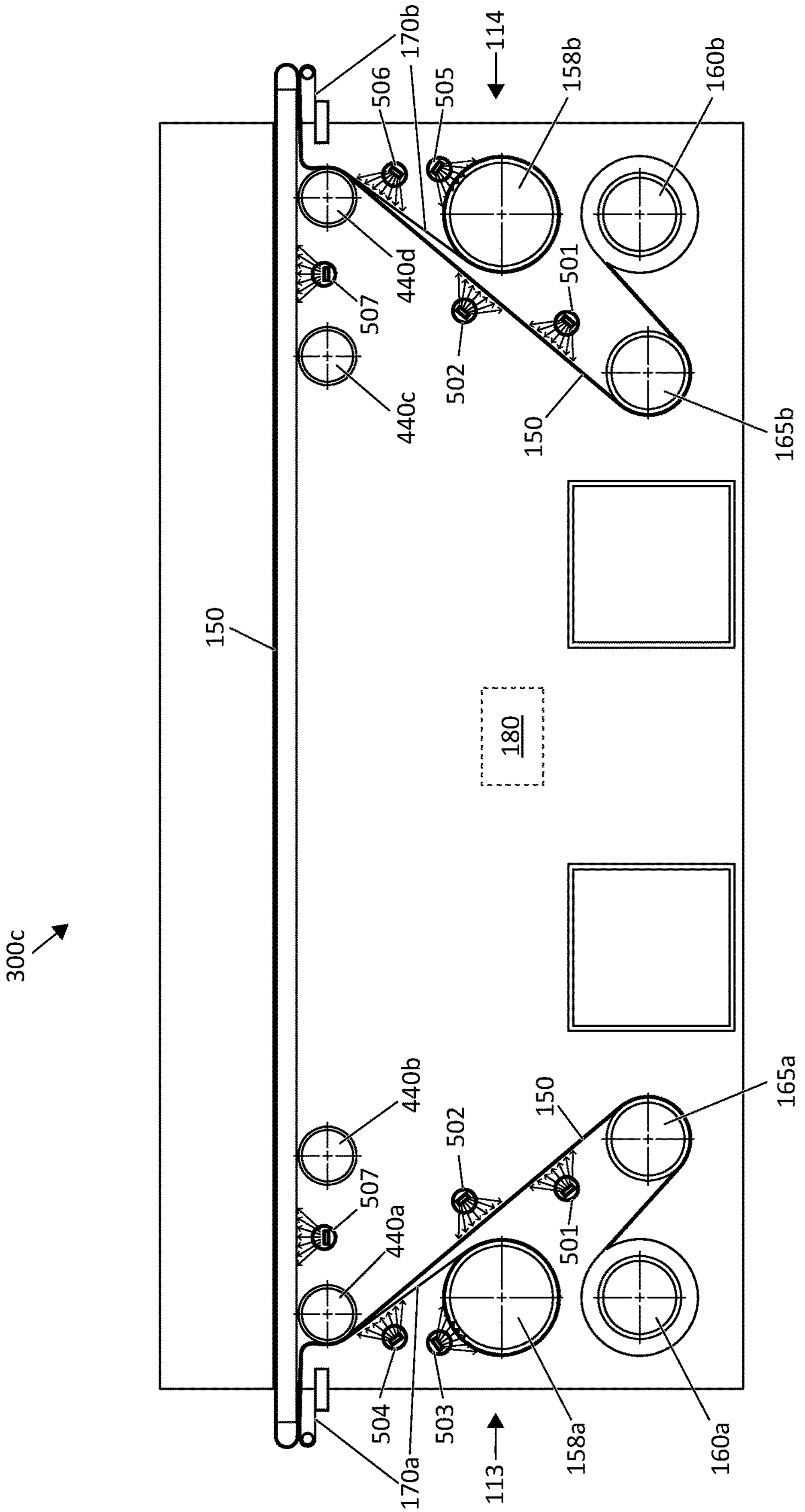
FIGS. 24A to 24D are schematic views of example cleaning components of the transfer device of FIGS. 7A to 7E.

For example, with reference to FIG. 24A, the transfer device 100 has several UV light emitters, including two UV light emitters 501 for emitting UV light on the upper surface of the first transfer belt 150, two UV light emitters 502 for emitting UV light on the lower surface of the first transfer belt 150, a UV light emitter 503 for emitting UV light on the upper surface of the second transfer belt 170*a*, a UV light emitter 504 for emitting UV light on the lower surface of the second transfer belt 170*a*, a UV light emitter 505 for emitting UV light on the upper surface of the third transfer belt 170*b*, and a UV light emitter 506 for emitting UV light on the lower surface of the third transfer belt 170*b*. Additionally, or alternatively, the transfer device 100 has at least one UV light emitter 507 for emitting UV light on the platform plate 210. Although a specific configuration with ten UV light emitters is shown, it is to be understood that other configurations are possible and are within the scope of the disclosure. The number of UV light emitters and their positioning within the transfer device 100 are implementation-specific.

In some implementations, the transfer device 100 has at least one fluid emitter configured to direct at least one of a cleaning fluid and a disinfectant fluid towards at least the upper surface of the transfer belt, or both an upper surface and a lower surface of the first transfer belt 150, as it passes by the fluid emitter(s). Additionally, or alternatively, at least one fluid emitter is positioned within the transfer device 100 to continuously or selectively emit fluid towards an upper surface and/or a lower surface of the second and third transfer belts 170*a-b* as they pass by the fluid emitter(s). Additionally, or alternatively, at least one fluid emitter is positioned within the transfer device 100 to continuously or selectively emit fluid towards the platform plate 210 as the platform plate 210 pass by the fluid emitter(s).

Figure 24B:
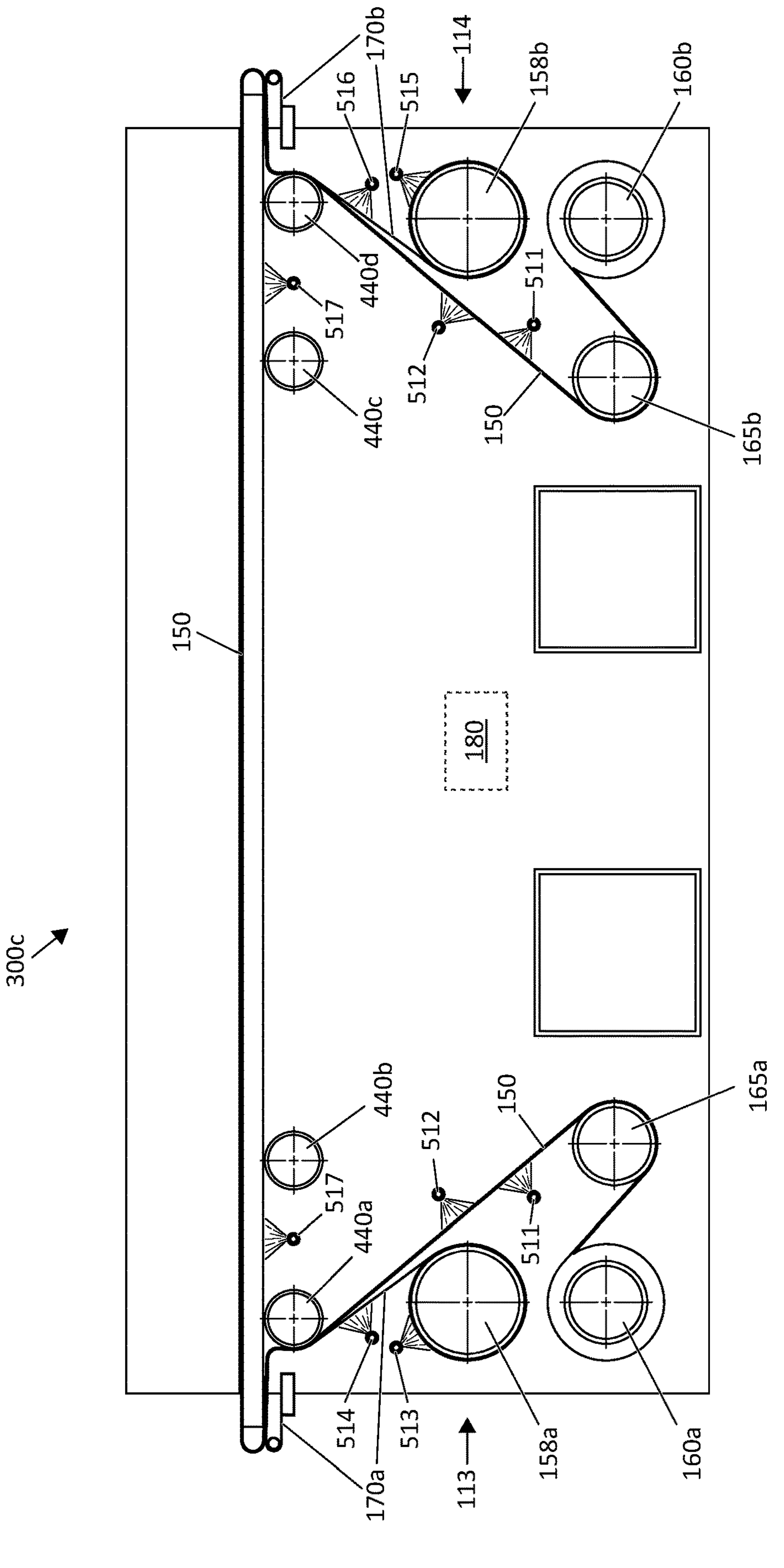

For example, with reference to FIG. 24B, the transfer device 100 has several fluid emitters, including two fluid emitters 511 for emitting fluid on the upper surface of the first transfer belt 150, two fluid emitters 512 for emitting fluid on the lower surface of the first transfer belt 150, a fluid emitter 513 for emitting fluid on the upper surface of the second transfer belt 170*a*, a fluid emitter 514 for emitting fluid on the lower surface of the second transfer belt 170*a*, a fluid emitter 515 for emitting fluid on the upper surface of the third transfer belt 170*b*, and a fluid emitter 516 for emitting fluid on the lower surface of the third transfer belt 170*b*. Additionally, or alternatively, the transfer device 100 has at least one fluid emitter 517 for emitting fluid on the platform plate 210. Although a specific configuration with ten fluid emitters is shown, it is to be understood that other configurations are possible and are within the scope of the disclosure. The number fluid emitters and their positioning within the transfer device 100 are implementation-specific.

In some implementations, the transfer device 100 has a fluid chamber defined within the housing interior, and a fluid agitator (e.g. an ultrasonic agitator or ultrasonic transducer) is provided therewith (e.g. inside the fluid chamber, coupled to an outside wall of the fluid chamber, or otherwise coupled to the fluid chamber) to continuously or selectively agitate a fluid within the fluid chamber as the first transfer belt 150 passes through the fluid chamber. Additionally, or alternatively, a fluid chamber and a fluid agitator provided therewith are positioned within the transfer device 100 to continuously or selectively agitate a fluid within the fluid chamber as the platform plate 210 passes through the fluid chamber. Such a configuration may be characterized as a fluid agitation system or as an ultrasonic bath system.

Figure 24C:
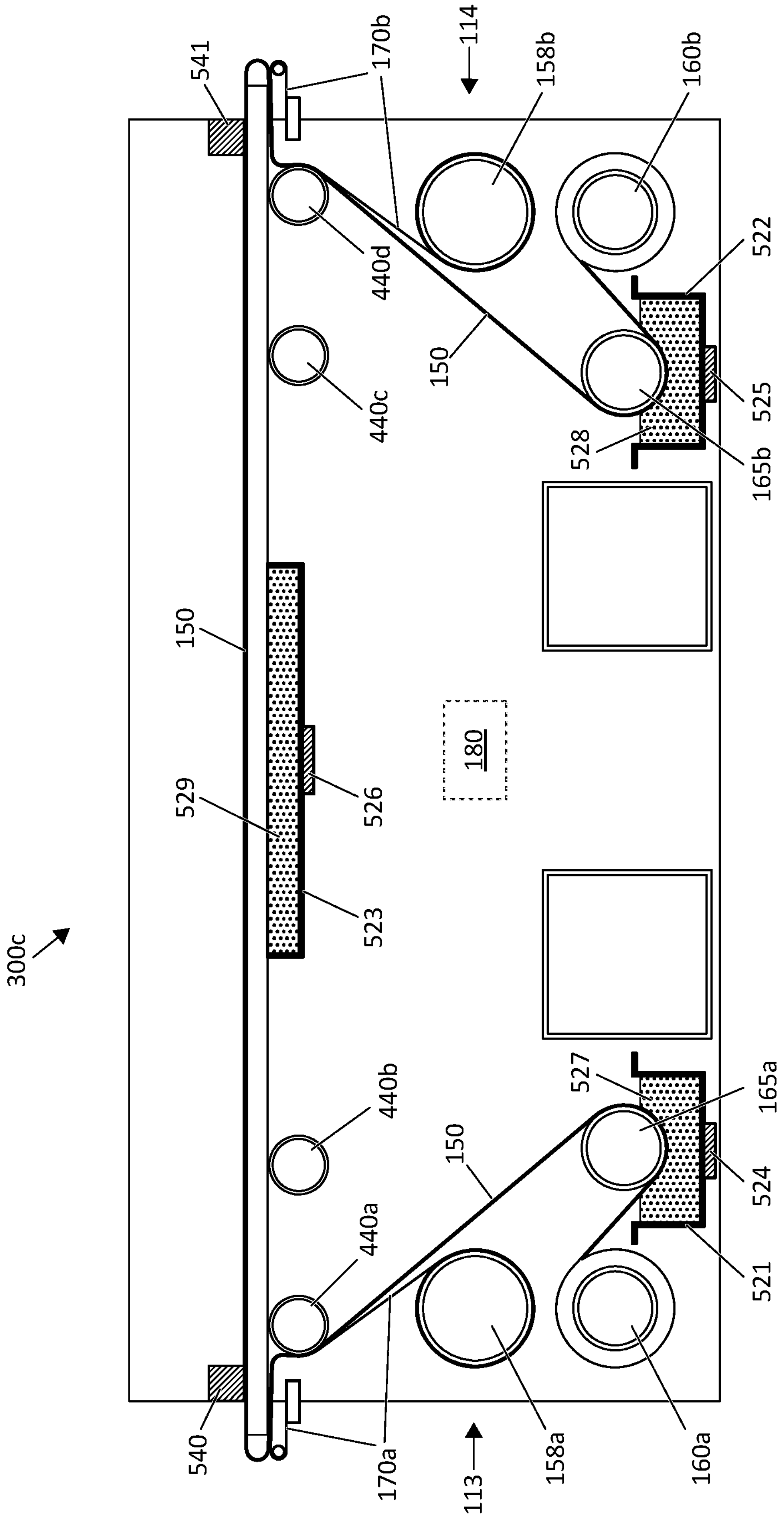

For example, with reference to FIG. 24C, the transfer device 100 has two fluid chambers 521-522 with fluid agitators 524-525 disposed therewith to continuously or selectively agitate a fluid within the two fluid chambers 521-522 as the first transfer belt 150 passes through the two fluid chambers 521-522. Additionally, or alternatively, the transfer device 100 has a third fluid chamber 523 with a fluid agitator 526 disposed therewith to continuously or selectively agitate a fluid within the third fluid chamber 523 as the platform plate 210 passes through the third fluid chamber 523.

In some implementations, a brush, sponge, microfiber, or other material may be positioned within the housing and in contact with a surface of the first transfer belt 150, such that when the transfer belt is advanced or retracted, dirt or debris may be removed from an upper surface of the first transfer belt 150, or both an upper surface and a lower surface of the first transfer belt 150. For example, with reference to FIG. 24C, in some implementations the transfer device 100 has a strip of contact material 540 and 541 (e.g. a brush, sponge, microfiber, or other material) disposed on either side of the device body to contact the upper side of the transfer belt 150. In some implementations the strips of contact material 540 and 541 on the side of the body are configured for easy replacement without the use of tools or the need to access the interior of the transfer device, for example by pulling off an old strip and pressing a new strip into place. Contact material may also be positioned at other locations within the housing of the transfer device 100.

Optionally, a reservoir of a cleaning and/or disinfectant fluid (e.g. alcohol, peroxide, bleach, etc.) may also be provided, for dispensing cleaning and/or disinfectant fluid onto the brush, sponge, microfiber, or other material, and/or directly onto the first transfer belt 150.

In some implementations, contact treatment can be combined with one or more other treatments for cleaning and/or disinfecting the platform or transfer belts. For example, with reference to FIG. 24C, the transfer device 100 has contact material 527-529 (e.g. a brush, sponge, microfiber, or other material) disposed within the fluid chambers 521-523. This contact material 527-529 is positioned to make contact with the first transfer belt 150 and/or the platform plate 210, and is configured to remove dirt or debris when such contact involves movement (e.g. when the first transfer belt 150 and/or the platform plate 210 are moving during operation). Other implementations are possible with the contact material 527-529 being disposed outside of the fluid chambers 521-523. The contact material and their positioning within the transfer device 100 are implementation-specific. In some implementations, contract treatment can also be combined with UV treatment and/or fluid spray treatment.

Figure 24D:
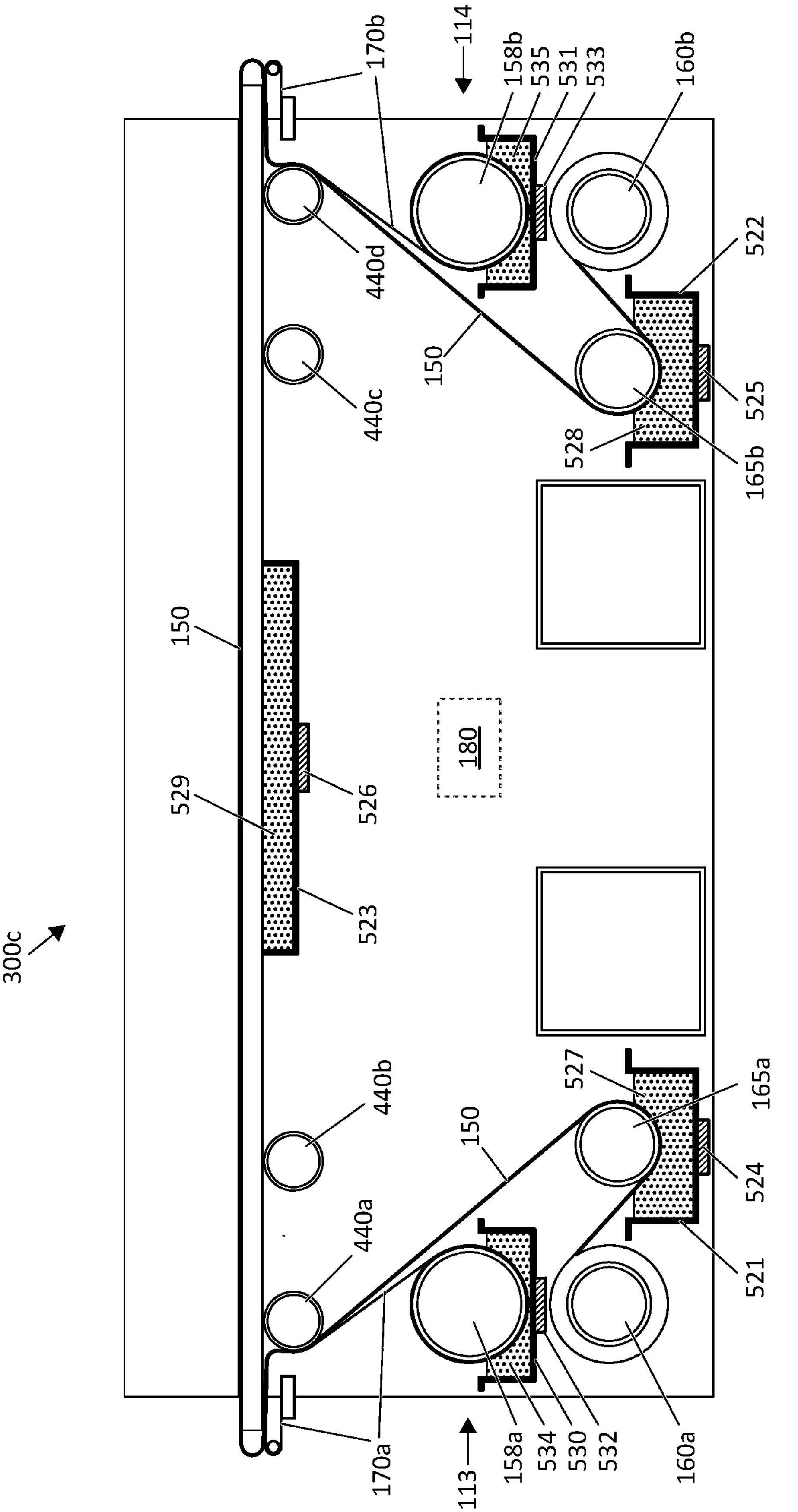

Although a specific configuration with three fluid chambers 521-523 and three fluid agitators 524-526 is shown in FIG. 24C, it is to be understood that other configurations are possible and are within the scope of the disclosure. The number fluid chambers and fluid agitators, and their positioning within the transfer device 100, are implementation-specific. For example, FIG. 24D shows an example implementation that is substantially the same as FIG. 24C, but with additional fluid chambers 530 and 531 positioned within the housing below rollers 155*a* and 158*b* for respectively cleaning and/or disinfecting the second and third transfer belts 170*a* and 170*b*. Each fluid chamber 350/351 has an associated agitator 352/353 and contact material 354/355 disposed therewith.

It will be appreciated that for implementations that include a fluid dispensing apparatus, 'fluid-proofing' or at least increased ingress protection may be implemented for fluid-sensitive parts of the device (e.g. electronics).

In some implementations, the transfer belt treatment system is operably coupled to the transfer device controller 180, and the transfer device controller 180 is configured to selectively actuate one or more of the UV light emitter 501-507, the fluid emitter 511-517, and the fluid agitator 524-256 concurrently or separately from each other. In some implementations, the transfer device controller is also operatively coupled to the platform plate treatment system, and the transfer device controller 180 is configured to selectively actuate one or more of the UV light emitter 501-507, the fluid emitter 511-517, and the fluid agitator 524-256 concurrently or separately from each other.

In some implementations, a manual actuator (e.g. a depressible button) may be provided to selectively actuate the transfer belt treatment system to provide one or more treatments (e.g. UV light, disinfectant fluid, ultrasonic bath agitation, contact treatment) to the transfer belt 150. For example, the UV light emitter may be configured such that, in response to depression of the manual actuator, it emits UV light for a pre-set period of time (e.g. 10 seconds, 30 minutes), which may be selected based on e.g. the decontamination level required, a distance of the emitter from belt 150, the intensity of light emitted by the emitter, and/or other factors known to those in the art. As another example, the agitator may be configured such that, in response to depression of the manual actuator, it agitates fluid in the chamber fora pre-set period of time (e.g. 10 seconds, 30 minutes), which may be selected based on e.g. the decontamination level required, composition of fluid within the chamber, and/or other factors known to those in the art. Additionally, or alternatively, the transfer belt treatment system may be configured such that one or more treatments (e.g. UV light, disinfectant fluid, ultrasonic agitation, contact treatment) are provided at pre-set intervals (e.g. following every transfer operation, every 24 hours) without requiring manual actuation, and/or at a preset time after a transfer operation has been performed.

Numerous modifications and variations of the present disclosure are possible in light of the above teachings. It is therefore to be understood that within the scope of the appended claims, the disclosure may be practised otherwise than as specifically described herein.

We claim:

1. A transfer device comprising:

a device body having a first end, a second end, a first side, and a second side; and a transfer platform comprising:

a platform plate having a first longitudinal end, a second longitudinal end, a first transverse edge extending between the first longitudinal end and the second longitudinal end, and a second transverse edge extending between the first longitudinal end and the second longitudinal end;

a platform lateral actuator configured to selectively move the platform plate laterally relative to the device body, such that the platform plate can be moved between a plurality of positions comprising (i) a stowed position in which the platform plate is retracted relative to the device body, (ii) a first extended position in which the first transverse edge is a leading edge that extends outward from the first side of the device body, and (iii) a second extended position in which the second transverse edge is a leading edge that extends outward from the second side of the device body;

a transfer belt having a first end secured to a first driven roller, a second end secured to a second driven roller, the belt extending from the first driven roller, around the first transverse edge of the platform plate, above an upper surface of the platform plate, around the second transverse edge of the platform plate, and to the second driven roller;

a first motor configured for driving the first driven roller, and a second motor configured for driving the second driven roller independent of the first driven roller; and a treatment system configured to apply a cleaning and/or disinfecting treatment to at least one of the transfer belt and the platform plate.

2. The transfer device of claim 1, wherein the transfer belt is a first transfer belt and the transfer device further comprises a second transfer belt extending below a bottom surface of the platform plate on the first side of the device body, and a third transfer belt extending below a bottom surface of the platform plate on the second side of the device body.

3. The transfer device of claim 2, further comprising:

a first locking mechanism configured to selectively attach the second transfer belt to the first transverse edge of the platform plate for the first extended position and to selectively detach the second transfer belt from the platform plate for the second extended position; and a second locking mechanism configured to selectively attach the third transfer belt to the second transverse edge of the platform plate for the second extended position and to selectively detach the third transfer belt from the platform plate for the first extended position.

4. The transfer device of claim 3, wherein:

the first locking mechanism is configured to selectively secure the second transfer belt to the device body for the second extended position; and the second locking mechanism is configured to selectively secure the third transfer belt to the device body for the first extended position.

5. The transfer device of claim 2, wherein the second transfer belt and the third transfer belt are attached to driven rollers.

6. The transfer device of claim 1, wherein the treatment system comprises a belt treatment system comprising at least one of:

an ultraviolet (UV) light emitter configured to direct UV light towards at least an upper surface of the transfer belt;

a fluid emitter configured to direct at least one of a cleaning fluid and a disinfectant fluid towards at least the upper surface of the transfer belt;

a fluid agitator configured to agitate fluid in a fluid chamber through which the transfer belt is configured to pass; and a contact material configured to contact at least an upper surface of the transfer belt.

7. The transfer device of claim 1, wherein the treatment system comprises a platform plate treatment system comprising at least one of:

a UV light emitter configured to direct UV light towards the platform plate;

a fluid emitter configured to direct at least one of a cleaning fluid and a disinfectant fluid towards the platform plate; and a fluid agitator configured to agitate fluid in a fluid chamber through which the platform plate is configured to pass.

8. The transfer device of claim 2, wherein the treatment system comprises a belt treatment system having:

a plurality of UV light emitters configured to direct UV light towards an upper surface of the first transfer belt, a lower surface of the first transfer belt, an upper surface of the second transfer belt, a lower surface of the second transfer belt, an upper surface of the third transfer belt, and a lower surface of the third transfer belt; and a plurality of fluid emitters configured to direct at least one of a cleaning fluid and a disinfectant fluid towards an upper surface of the first transfer belt, a lower surface of the first transfer belt, an upper surface of the second transfer belt, a lower surface of the second transfer belt, an upper surface of the third transfer belt, and a lower surface of the third transfer belt.

9. The transfer device of claim 2, wherein the treatment system comprises:

a plurality of fluid chambers, each fluid chamber filled with a fluid and a contact material and having a fluid agitator disposed therewith, wherein the plurality of fluid chambers comprise at least one fluid chamber positioned to receive each of the platform, the first transfer belt, the second transfer belt, and the third transfer belt.

10. The transfer device of claim 1, wherein the treatment system comprises contact material positioned to make contact with the first transfer belt and/or the platform plate, and is configured to remove dirt or debris when such contact involves movement.

11. The transfer device of claim 1, wherein the device body has a width between the first and second sides of the device body, and wherein, in the first and second extended positions, the platform plate extends outward by a distance that is equal to the width of the device body plus or minus 25%.

12. The transfer device of claim 11, wherein the width of the device body is between 400 mm to 1000 mm, and wherein, in the first and second extended positions, the platform plate extends outwards by 360 mm to 1250 mm.

13. The transfer device of claim 1, wherein the width of the device body is between 400 mm to 1250 mm, and wherein, in the first and second extended positions, the platform plate extends outwards by 440 mm to 1600 mm.

14. The transfer device of claim 1, further comprising a device support structure secured to the device body for supporting the device body above a floor surface, wherein the device support structure is configurable to adjust a height of the device body above the floor surface and/or an angle of the device body.

15. The transfer device of claim 14, wherein the device support structure comprises a plurality of wheels to facilitate translation of the transfer device across the floor surface.

16. The transfer device of claim 15, wherein at least one of the plurality of wheels is driven by a motor, such that the transfer device is able to transport itself across the floor surface.

17. The transfer device of claim 1, further comprising:

a transfer device controller configured to control the transfer platform including at least the platform lateral actuator of the platform plate.

18. The transfer device of claim 17, wherein the first driven roller and the second driven roller for the transfer belt are operably coupled to the transfer device controller, and the transfer device controller is configured to selectively actuate the first driven roller and the second driven roller concurrently or separately from each other.

19. The transfer device of claim 6, further comprising a transfer device controller configured to control the transfer platform including at least the platform lateral actuator of the platform plate, wherein the belt treatment system comprises at least two of the UV light emitter, the fluid emitter, and the fluid agitator and is operably coupled to the transfer device controller, and the transfer device controller is configured to selectively actuate the at least two of the UV light emitter, the fluid emitter, and the fluid agitator concurrently or separately from each other.

20. The transfer device of claim 7, further comprising a transfer device controller configured to control the transfer platform including at least the platform lateral actuator of the platform plate, wherein the platform plate treatment system comprises at least two of the UV light emitter, the fluid emitter, and the fluid agitator and is operatively coupled to the transfer device controller, and wherein the transfer device controller is configured to selectively actuate the at least two of the UV light emitter, the fluid emitter, and the fluid agitator concurrently or separately from each other.

21. The transfer device of claim 14, further comprising a transfer device controller configured to control the transfer platform including at least the platform lateral actuator of the platform plate, wherein the device support structure is operatively coupled to the transfer device controller, and wherein the transfer device controller is configured to adjust the height of the device body above the floor surface and/or the angle of the device body.

22. The transfer device of claim 17, wherein the transfer device comprises a plurality of controllable subsystems, and wherein the transfer device controller comprises a single controller configured to control the transfer platform and all of the controllable subsystems.

* * * * *